US012706199B1

(12) United States Patent
Burdine

(10) Patent No.: US 12,706,199 B1
(45) Date of Patent: Aug. 11, 2026

(54) METHOD, APPARATUS, AND COMPUTER PROGRAM PRODUCT FOR USING MACHINE LEARNING TO GENERATE AN OFFSET AMOUNT

(71) Applicant: McKesson Corporation, Irving, TX (US)

(72) Inventor: Jared Burdine, Dunwoody, GA (US)

(73) Assignee: McKesson Corporation, Irving, TX (US)

( * ) Notice: Subject to any disclaimer, the term of this patent is extended or adjusted under 35 U.S.C. 154(b) by 838 days.

(21) Appl. No.: 17/491,870

(22) Filed: Oct. 1, 2021

(51) Int. Cl.
*G16H 20/10* (2018.01)
*G06N 20/00* (2019.01)

(52) U.S. Cl.
CPC ............ *G16H 20/10* (2018.01); *G06N 20/00* (2019.01)

(58) Field of Classification Search
CPC ...................................................... G16H 20/10
See application file for complete search history.

(56) References Cited

U.S. PATENT DOCUMENTS

| | | | |
|---|---|---|---|
| 5,012,035 | A | 4/1991 | Sartori et al. |
| 5,173,851 | A | 12/1992 | Off et al. |
| 5,595,342 | A | 1/1997 | McNair et al. |
| 5,628,530 | A | 5/1997 | Thornton |
| 5,726,092 | A | 3/1998 | Mathews et al. |
| 5,757,898 | A | 5/1998 | Nishikawa |
| 5,769,228 | A | 6/1998 | Wroblewski |

(Continued)

FOREIGN PATENT DOCUMENTS

| | | | |
|---|---|---|---|
| AU | 2003243327 | A | 12/2003 |
| CA | 2 482 370 | A1 | 3/2006 |

(Continued)

OTHER PUBLICATIONS

Davies, Rory, "Specialty drugs: Four options for managing costs: with specialty drug costs growing at a double-digit pace and new drugs entering the market, plan sponsors struggle to keep up. The author describes challenges plan sponsors face with some particular high-cost drugs and offers four cost-control strategies", Essay, *Benefits Magazine*, Jun. 2017, 9 pages, vol. 54, No. 6, International Foundation of Employee Benefit Plans, US.

(Continued)

*Primary Examiner* — Jay M. Patel
(74) *Attorney, Agent, or Firm* — Alston & Bird LLP

(57) ABSTRACT

A method, apparatus and computer program product are provided for generating offset amounts for inquiry data objects received over a network. Machine learning algorithms may be used to determine the offset amount, based on a base quantitative amount, a product identifier, and a longevity indicator. Historical data may be modelled and analyzed to determine relationships between quantitative amounts, longevity indicators, and adherence data. Adherence may therefore be improved by generating an offset amount dependent on the machine learning algorithms and model. By utilizing a model and machine learning algorithms, the model may account for new products, different pricing structures, and/or the like, and may enable the efficient generation of offset amounts for hundreds or thousands of products in an efficient manner, and for different associated longevities.

8 Claims, 2 Drawing Sheets

(56) References Cited

U.S. PATENT DOCUMENTS 6,012,035 A 1/2000 Freeman et al.
6,111,218 A 8/2000 Akers et al.
6,463,462 B1 10/2002 Smith et al.
6,595,342 B1 7/2003 Maritzen et al.
6,726,092 B2 4/2004 Goldberg et al.
6,757,898 B1 6/2004 Ilsen et al.
6,769,228 B1 8/2004 Mahar
7,155,397 B2 12/2006 Alexander et al.
7,192,741 B2 3/2007 Otte et al.
7,337,129 B1 2/2008 Lowry et al.
7,346,768 B2 3/2008 DiRienzo
7,409,632 B1 8/2008 DiRienzo
7,426,476 B2 9/2008 Munoz et al.
7,734,483 B1 6/2010 Smith et al.
7,783,383 B2 8/2010 Eliuk et al.
7,840,424 B2 11/2010 Wiley et al.
7,856,364 B1 12/2010 Wiley et al.
7,912,741 B1 3/2011 Pinsonneault
7,921,021 B1 4/2011 Newman
8,036,913 B1 10/2011 Pinsonneault et al.
8,036,914 B1 10/2011 Pinsonneault
8,036,918 B1 10/2011 Pinsonneault
8,050,943 B1 11/2011 Wiley et al.
8,060,379 B1 11/2011 Pinsonneault et al.
8,126,743 B1 2/2012 Wilk
8,326,773 B1 12/2012 Bellamy
8,346,571 B2 1/2013 Kalies, Jr.
8,412,537 B1 4/2013 Fenton et al.
8,442,847 B1 5/2013 Shrivastava
8,489,415 B1 7/2013 Ringold
8,521,557 B1 8/2013 Ringold et al.
8,538,777 B1 9/2013 Kaye et al.
8,560,340 B1 10/2013 Ringold
8,639,523 B1 1/2014 Pinsonneault
8,645,162 B2 2/2014 Boerger et al.
8,671,018 B2 3/2014 Thomas et al.
8,712,797 B1 4/2014 Bezdek et al.
8,738,399 B1 5/2014 Abou Nader et al.
8,786,650 B1 7/2014 Eller et al.
8,799,018 B1 8/2014 Rea et al.
8,984,059 B2 3/2015 Johnson
9,026,507 B2 5/2015 Shraim et al.
9,100,793 B2 8/2015 Johnson
9,171,322 B2 10/2015 Spievak et al.
9,356,947 B2 5/2016 Shraim et al.
9,760,871 B1 9/2017 Pourfallah et al.
9,779,129 B1 10/2017 Lequeux
9,786,023 B2 10/2017 Cohan et al.
10,109,027 B1 10/2018 Stack
10,157,262 B1 12/2018 Pinsonneault
10,262,383 B1 4/2019 Harris, Sr. et al.
10,331,855 B1 6/2019 Bratton et al.
10,417,380 B1 9/2019 Kaye et al.
10,423,759 B1 9/2019 Harris, Sr. et al.
10,489,552 B2 11/2019 Pinsonneault
10,496,793 B1 12/2019 Lawrence et al.
10,565,656 B1 2/2020 Pinsonneault et al.
10,606,984 B1 3/2020 Kaye et al.
10,616,146 B1 4/2020 Hopkins et al.
10,628,797 B2 4/2020 Shraim et al.
10,642,812 B1 5/2020 Hopkins et al.
10,713,694 B1 7/2020 Harris et al.
10,747,848 B2 8/2020 Guinan
10,778,618 B2 9/2020 Karnin et al.
10,862,832 B1 12/2020 Harris
10,924,545 B2 2/2021 Momchilov et al.
10,924,585 B1 2/2021 Harris et al.
10,929,932 B1 2/2021 Golden et al.
10,978,198 B1 4/2021 Pinsonneault
10,999,224 B1 5/2021 Frechen et al.
11,043,293 B1 6/2021 Salzbrenner
11,170,394 B1 11/2021 Macinski
11,398,992 B1 7/2022 Frechen et al.
11,418,468 B1 8/2022 Harris
11,443,835 B1 9/2022 Gangaikondan-Iyer et al.
11,508,471 B1 11/2022 Anselmi et al.
11,514,137 B1 11/2022 Kaye et al.
11,562,437 B1 1/2023 Hopkins et al.
11,587,657 B2 2/2023 Hopkins et al.
11,610,240 B1 * 3/2023 Burdine ................. G16H 40/20
11,636,548 B1 4/2023 Hopkins et al.
11,640,618 B1 * 5/2023 Burdine ............. G06Q 30/0206
705/14.15
12,165,756 B1 12/2024 Kaye et al.
12,197,972 B1 1/2025 Hopkins
2001/0029483 A1 10/2001 Schultz et al.
2001/0034613 A1 10/2001 Rubsamen
2001/0037216 A1 11/2001 Oscar et al.
2001/0039589 A1 11/2001 Aho et al.
2001/0056359 A1 12/2001 Abreu
2002/0002495 A1 1/2002 Ullman
2002/0004812 A1 1/2002 Motoyama
2002/0032582 A1 3/2002 Feeney et al.
2002/0032583 A1 3/2002 Joao
2002/0035484 A1 3/2002 McCormick
2002/0087583 A1 7/2002 Morgan et al.
2002/0111832 A1 8/2002 Judge
2002/0133379 A1 9/2002 Lewis et al.
2002/0143579 A1 10/2002 Docherty et al.
2002/0147614 A1 10/2002 Doerr et al.
2002/0188552 A1 12/2002 Kavounas et al.
2002/0198831 A1 12/2002 Patricelli et al.
2003/0009367 A1 1/2003 Morrison
2003/0050796 A1 3/2003 Baldwin
2003/0050799 A1 3/2003 Jay et al.
2003/0069760 A1 4/2003 Gelber
2003/0074234 A1 4/2003 Stasny
2003/0097310 A1 5/2003 Ono et al.
2003/0130875 A1 7/2003 Hawash et al.
2003/0149625 A1 8/2003 Leonardi et al.
2003/0154163 A1 8/2003 Phillips et al.
2003/0172008 A1 9/2003 Hage et al.
2003/0187690 A1 10/2003 Miller
2003/0229540 A1 12/2003 Algiene
2003/0236747 A1 12/2003 Sager
2004/0006490 A1 1/2004 Gingrich et al.
2004/0039599 A1 2/2004 Fralic
2004/0054685 A1 3/2004 Rahn et al.
2004/0059607 A1 3/2004 Ball et al.
2004/0073456 A1 4/2004 Gottlieb et al.
2004/0073457 A1 4/2004 Kalies
2004/0078222 A1 4/2004 Khan et al.
2004/0078234 A1 4/2004 Tallal, Jr.
2004/0088187 A1 5/2004 Chudy et al.
2004/0103062 A1 5/2004 Wood et al.
2004/0117323 A1 6/2004 Mindala
2004/0148198 A1 7/2004 Kalies
2004/0153336 A1 8/2004 Virdee et al.
2004/0199545 A1 10/2004 Wagner et al.
2004/0236630 A1 11/2004 Kost et al.
2004/0249745 A1 12/2004 Baaren
2005/0015280 A1 1/2005 Gabel et al.
2005/0060201 A1 3/2005 Connely, III et al.
2005/0065821 A1 3/2005 Kalies, Jr.
2005/0075932 A1 4/2005 Mankoff
2005/0080692 A1 4/2005 Padam et al.
2005/0102169 A1 5/2005 Wilson
2005/0154627 A1 7/2005 Zuzek et al.
2005/0187793 A1 8/2005 Myles
2005/0197862 A1 9/2005 Paterson et al.
2005/0240442 A1 10/2005 Lapsker et al.
2005/0240473 A1 10/2005 Ayers, Jr. et al.
2005/0261939 A1 11/2005 Augspurger et al.
2005/0288972 A1 12/2005 Marvin et al.
2006/0020514 A1 1/2006 Yered
2006/0026041 A1 2/2006 Ullman
2006/0036470 A1 2/2006 Oaks
2006/0085231 A1 4/2006 Brofman
2006/0085385 A1 4/2006 Foster et al.
2006/0113376 A1 6/2006 Reed et al.
2006/0149595 A1 7/2006 Williams et al.
2006/0149784 A1 7/2006 Tholl et al.
2006/0155578 A1 7/2006 Eisenberger et al.
2006/0184391 A1 8/2006 Barre et al.

(56) References Cited

U.S. PATENT DOCUMENTS

2006/0212318 A1 9/2006 Dooley
2006/0212345 A1 9/2006 Soza et al.
2006/0224414 A1 10/2006 Astrup et al.
2006/0224417 A1 10/2006 Werner
2006/0224443 A1 10/2006 Soza et al.
2006/0235747 A1 10/2006 Hammond et al.
2006/0259363 A1 11/2006 Jhetam et al.
2007/0005402 A1 1/2007 Kennedy et al.
2007/0033137 A1 2/2007 Provost et al.
2007/0043589 A1 2/2007 Warren et al.
2007/0043595 A1 2/2007 Pederson
2007/0050209 A1 3/2007 Yered
2007/0050210 A1 3/2007 Wiley, II
2007/0067186 A1 3/2007 Brenner et al.
2007/0094133 A1 4/2007 Anandarao et al.
2007/0108053 A1 5/2007 Cramer et al.
2007/0136100 A1 6/2007 Daugherty et al.
2007/0162303 A1 7/2007 Wiley et al.
2007/0168228 A1 7/2007 Lawless
2007/0185799 A1 8/2007 Harrison et al.
2007/0191985 A1 8/2007 Bain
2007/0194352 A1 8/2007 Han
2007/0202886 A1 8/2007 Dhebri et al.
2007/0204043 A1 8/2007 Espinosa et al.
2007/0219813 A1 9/2007 Moore
2007/0233525 A1 10/2007 Boyle
2007/0233526 A1 10/2007 Hoffman et al.
2007/0239493 A1 10/2007 Sweetland et al.
2007/0250341 A1 10/2007 Howe et al.
2007/0260750 A1 11/2007 Feied et al.
2007/0276697 A1 11/2007 Wiley, II et al.
2007/0294765 A1 12/2007 Rihn et al.
2007/0299915 A1 12/2007 Shraim et al.
2008/0033750 A1 2/2008 Swiss et al.
2008/0103836 A1 5/2008 Park et al.
2008/0112411 A1 5/2008 Stafford et al.
2008/0152107 A1 6/2008 Mendiola
2008/0183492 A1 7/2008 Warren et al.
2008/0215361 A1 9/2008 Nunnari et al.
2008/0262948 A1 10/2008 Grady et al.
2009/0006141 A1 1/2009 Karr
2009/0030719 A1 1/2009 Nadas et al.
2009/0064330 A1 3/2009 Shraim et al.
2009/0083064 A1 3/2009 Mahinda
2009/0094051 A1 4/2009 Ard et al.
2009/0100099 A1 4/2009 Buckwalter
2009/0106313 A1 4/2009 Boldyga
2009/0112707 A1 4/2009 Weiss et al.
2009/0198510 A1 8/2009 Ditto
2009/0204477 A1 8/2009 Urso
2009/0287558 A1 11/2009 Seth et al.
2009/0313112 A1 12/2009 Champ et al.
2009/0327363 A1 12/2009 Cullen et al.
2010/0030667 A1 2/2010 Chudy et al.
2010/0057640 A1 3/2010 Cannata
2010/0070298 A1 3/2010 Kalies
2010/0144259 A1 6/2010 Allexon et al.
2010/0145730 A1 6/2010 Abreu
2010/0161353 A1 6/2010 Mayaud
2010/0217622 A1 8/2010 Brown et al.
2010/0249045 A1 9/2010 Babul
2010/0285821 A1 11/2010 Smeeding et al.
2010/0287001 A1 11/2010 Pearce et al.
2010/0293236 A1 11/2010 Wisner et al.
2011/0015978 A1 1/2011 Welch, Jr.
2011/0112871 A1 5/2011 Simonowski et al.
2011/0161109 A1 6/2011 Pinsonneault et al.
2011/0196697 A1 8/2011 Akers
2011/0288886 A1 11/2011 Whiddon et al.
2011/0288925 A1 11/2011 Thomas et al.
2012/0053958 A1 3/2012 Marshall et al.
2012/0109839 A1 5/2012 Anderson et al.
2012/0136809 A1 5/2012 Cannata et al.
2012/0143627 A1 6/2012 Ruben et al.
2012/0166268 A1 6/2012 Griffiths
2012/0179481 A1 7/2012 Patel et al.
2012/0185263 A1 7/2012 Emert
2012/0185264 A1 7/2012 Demogenes et al.
2012/0232983 A1 9/2012 Bertha et al.
2012/0253829 A1 10/2012 John et al.
2012/0253830 A1 10/2012 John et al.
2012/0253831 A1 10/2012 John et al.
2012/0253832 A1 10/2012 John et al.
2012/0253833 A1 10/2012 John et al.
2012/0253846 A1 10/2012 John et al.
2012/0265591 A1 10/2012 Hwang
2012/0303382 A1* 11/2012 Paul ........................ G16H 20/10 705/2
2012/0323608 A1 12/2012 Herzlinger
2013/0041968 A1 2/2013 Cohen et al.
2013/0046610 A1 2/2013 Abraham
2013/0103602 A1 4/2013 Melnick et al.
2013/0144715 A1 6/2013 Kranzley et al.
2013/0179180 A1 7/2013 Patra
2013/0191147 A1 7/2013 Harrell
2013/0197980 A1 8/2013 Lerner et al.
2013/0246082 A1 9/2013 Brylawski et al.
2013/0311389 A1 11/2013 Kaehler et al.
2014/0039911 A1 2/2014 Iyer
2014/0088985 A1 3/2014 Grant et al.
2014/0214435 A1 7/2014 Previdi
2014/0249861 A1 9/2014 Gamble et al.
2014/0249864 A1 9/2014 Sultan et al.
2014/0278448 A1 9/2014 Sadeghi et al.
2014/0278456 A1 9/2014 Milosevich et al.
2014/0278531 A1 9/2014 Gupta
2015/0032465 A1 1/2015 Sundar et al.
2015/0088557 A1 3/2015 Huynh et al.
2015/0142479 A1 5/2015 Porter et al.
2015/0149197 A1 5/2015 Guinan
2015/0154565 A1 6/2015 Kaehler et al.
2015/0154588 A1 6/2015 Purves et al.
2015/0195224 A1 7/2015 Karnin et al.
2015/0213195 A1 7/2015 Blechman
2015/0234991 A1 8/2015 Pinsonneault
2015/0235177 A1 8/2015 Shraim et al.
2015/0269695 A1 9/2015 Pinsonneault et al.
2015/0278472 A1* 10/2015 King ...................... G16H 20/10 705/2
2015/0332422 A1 11/2015 Gilmartin
2015/0356255 A1 12/2015 Simpson et al.
2015/0371000 A1 12/2015 Pinsonneault
2016/0012465 A1 1/2016 Sharp
2016/0103978 A1 4/2016 Stong
2016/0140593 A1 5/2016 Smeeding et al.
2016/0188820 A1 6/2016 Brown et al.
2016/0213512 A1 7/2016 Palanker et al.
2016/0267544 A1 9/2016 Flood et al.
2016/0267545 A1 9/2016 Glass et al.
2016/0307195 A1 10/2016 Cantwell et al.
2016/0321406 A1 11/2016 Timmerman et al.
2016/0321410 A1 11/2016 Timmerman et al.
2016/0358142 A1 12/2016 Hillen
2016/0358293 A1 12/2016 Berger et al.
2016/0359795 A1 12/2016 Fehling
2017/0034087 A1 2/2017 Borenstein et al.
2017/0039331 A1 2/2017 Bezdek et al.
2017/0220768 A1 8/2017 Tanner, Jr. et al.
2017/0255759 A1 9/2017 McGrath
2017/0323295 A1 11/2017 Kranzley et al.
2017/0324695 A1 11/2017 Fischer et al.
2017/0329922 A1 11/2017 Eberting et al.
2018/0012244 A1 1/2018 Leonardi
2018/0075212 A1 3/2018 Kubey
2018/0075215 A1* 3/2018 Loiacono ............... G16H 40/20
2018/0366810 A1 12/2018 Nero et al.
2019/0095582 A1 3/2019 Waits
2019/0213212 A1 7/2019 Adato et al.
2019/0252049 A1 8/2019 Fotsch et al.
2019/0348160 A1 11/2019 Heavelyn
2019/0371444 A1* 12/2019 Glass ..................... G16H 20/10
2019/0385733 A1 12/2019 Kaye et al.
2019/0385734 A1 12/2019 Pinsonneault
2020/0105392 A1 4/2020 Karkazis et al.

(56) References Cited

U.S. PATENT DOCUMENTS

| | | | | |
|---|---|---|---|---|
| 2020/0143946 | A1* | 5/2020 | Lewis | G16H 15/00 |
| 2020/0242626 | A1 | 7/2020 | Agarwal | |
| 2020/0372988 | A1 | 11/2020 | Bezdek et al. | |
| 2020/0395114 | A1 | 12/2020 | Bachwani | |
| 2021/0217044 | A1 | 7/2021 | Sigsbee | |
| 2021/0287774 | A1 | 9/2021 | Curtiss et al. | |
| 2021/0319887 | A1 | 10/2021 | Derrick, Jr. et al. | |
| 2021/0374872 | A1 | 12/2021 | Stewart et al. | |
| 2021/0374876 | A1 | 12/2021 | Cedergreen | |
| 2021/0407642 | A1 | 12/2021 | Xia et al. | |

FOREIGN PATENT DOCUMENTS

| | | | |
|---|---|---|---|
| CA | 2792252 | A1 | 4/2013 |
| CA | 2810686 | A1 | 10/2013 |
| CN | 102362778 | | 2/2012 |
| KR | 100755440 | | 9/2007 |
| KR | 101038074 | | 6/2011 |
| KR | 101101692 | | 12/2011 |
| KR | 20110138108 | | 12/2011 |
| KR | 20110138572 | | 12/2011 |
| KR | 101154858 | | 6/2012 |
| WO | WO 1991/006917 | A1 | 5/1991 |
| WO | WO 1995/003569 | A2 | 2/1995 |
| WO | WO 1997/025682 | A1 | 7/1997 |
| WO | WO 1998/050871 | A1 | 11/1998 |
| WO | WO 2000/039737 | A1 | 7/2000 |
| WO | WO 2003/098401 | A2 | 11/2003 |
| WO | WO 2007/025295 | A2 | 3/2007 |
| WO | WO 2007/094772 | A1 | 8/2007 |
| WO | WO 2008/092109 | A2 | 7/2008 |

OTHER PUBLICATIONS

United States Patent and Trademark Office, Notice of Allowance received for U.S. Appl. No. 16/797,277, dated Dec. 21, 2022, 26 pages, US.

U.S. Appl. No. 16/797,277, "Method, Apparatus, and Computer Program Product for Partitioning Prescription Transaction Costs in an Electronic Prescription Transaction", Unpublished (filing date Feb. 21, 2020), (Jared Burdine, Inventor), (McKesson Corporation, Assignee).

United States Patent and Trademark Office, Non-Final Office Action received for U.S. Appl. No. 16/797,277, dated May 17, 2022, 17 pages, US.

United States Patent and Trademark Office, Final Office Action received for U.S. Appl. No. 16/797,277, dated Sep. 12, 2022, 23 pages, US.

Pharmacy Reject Codes NCPDP, 5 pages.

St. Vincent's first to use Birmingham startup's information system. The Birmingham News [Online] Apr. 11, 2005. URL: http://www.awarix.com.

St. Vincent's is Digital Flagship D. Lockridge; Birmingham Medical News [Online] Sep. 2005.

Two automatic identification technology, neither new in the sense if being recent developments . . . Patient Safety & Quality Healthcare [Online] Aug. 2005_ URL: http://www_awarix.com.

Advisory Action for U.S. Appl. No. 14/193,294 mailed Nov. 9, 2017, 3 pages.

Advisory Action for U.S. Appl. No. 15/085,166 dated Apr. 11, 2019, 4 pages.

Advisory Action for U.S. Appl. No. 15/085,166 dated Apr. 29, 2020, 3 pages.

Advisory Action for U.S. Appl. No. 15/137,371 mailed Feb. 25, 2019, 5 pages.

Advisory Action for U.S. Appl. No. 15/427,746 mailed Jul. 2, 2019, 2 pages.

Advisory Action received for U.S. Appl. No. 15/085,166, dated Jan. 29, 2021, 3 pages, US.

Almaro, Moshe; "Recovery and Reuse of Unused Prescription Drugs" MIT What Matters: Aug. 2005.

American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.

American Society of Health-System Pharmacists (ASHP), "Is Prescribing the Next Step in the Evolution of Pharmacy?" May 15, 2012.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Anonymous, Medic; On-line Goes In-House, Chain Store Age Executive, Jan. 1987, vol. 63, Issue 1, USA; Abstract only.

Anonymous, Pharmacy Industry Leaders Launch Firm to Supply Real-Time Data, PR Newswire, Jul. 30, 2001, p. 1, New York, NY, USA.

Anonymous, TechRx Announces Successful Beta Deployment of T-Rex. PR Newswire. May 13, 2002.

Bowman, Michelle, et al., "Risk Assessment of Pharmacies & Electronic Prescriptions," 2019 IEEE/ACM International Conference on Advances in Social Networks Analysis and Mining (ASONAM), Aug. 27-30, 2019, pp. 641-644, Vancouver, BC, Canada.

California Health Care Foundation, "When the Price Is Not Right: State Options on Prescription Drug Pricing", dated Jun. 2016, retrieved from the Internet at: <URL: https://www.chcf.org/wp-content/uploads/2017/12/PDF-WhenStateRxPricing.pdf>, 16 pages.

Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.

Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central LTD, UK.

CMS Updates Drug Dashboards with Prescription Drug Pricing and Spending Data, Data, Medicare Part D, Prescription drugs (Mar. 14, 2019).

Coase, R. H., "The Nature of the Firm", Economica, Nov. 1937, pp. 386-405, vol. 4, No. 16, Blackwell Publishing for London School of Economics and Political Science, retrieved from the Internet at http://www.jstor.org/stable/2626876 on Nov. 7, 2011.

Consalvo, Bob; "City of Boston in the City Council" hearing notice, Dec. 6, 2006.

Coping with Information Overload. The News Source for Healthcare Information Technology [Online] Nov. 2004. URL: http://www.awarix.com.

Decision to Grant European Patent Application No. 13809457.8 dated May 18, 2017.

Dubois, Robert W., "Rx Drug Costs: List Prices Versus Net Prices and the Importance of Staying Within the Data", Health Affairs Blog, Mar. 2019, 7 pages.

Examiner's Answer for U.S. Appl. No. 14/145,027 mailed Sep. 7, 2016, 27 pages.

Extended European Search Report for European Application No. 13809457.8 dated Apr. 15, 2016, 6 pages.

Final Office Action for U.S. Appl. No. 12/140,015 mailed Jan. 31, 2011, 10 pages.

Final Office Action for U.S. Appl. No. 12/415,062 mailed Oct. 6, 2011, 18 pages.

Final Office Action for U.S. Appl. No. 12/555,589 mailed Apr. 11, 2012, 17 pages.

Final Office Action for U.S. Appl. No. 12/560,071 mailed Aug. 28, 2015, 8 pages.

Final Office Action for U.S. Appl. No. 12/560,071 mailed Nov. 8, 2012, 11 pages.

Final Office Action for U.S. Appl. No. 12/570,982 mailed Apr. 11, 2014, 22 pages.

Final Office Action for U.S. Appl. No. 12/570,982 mailed Aug. 28, 2015, 10 pages.

(56) References Cited

OTHER PUBLICATIONS

Final Office Action for U.S. Appl. No. 12/570,982 mailed Jan. 17, 2013, 19 pages.
Final Office Action for U.S. Appl. No. 12/730,015 mailed Aug. 14, 2012, 10 pages.
Final Office Action for U.S. Appl. No. 12/978,898 mailed May 16, 2013, 16 pages.
Final Office Action for U.S. Appl. No. 13/721,890 mailed Jun. 24, 2015, 14 pages.
Final Office Action for U.S. Appl. No. 13/721,890 mailed Nov. 25, 2016, 12 pages.
Final Office Action for U.S. Appl. No. 13/782,909 mailed May 31, 2016, 18 pages.
Final Office Action for U.S. Appl. No. 13/782,909 mailed Oct. 6, 2015, 24 pages.
Final Office Action for U.S. Appl. No. 13/804,175 mailed Oct. 6, 2015, 6 pages.
Final Office Action for U.S. Appl. No. 13/827,676 mailed Jul. 13, 2015, 17 pages.
Final Office Action for U.S. Appl. No. 14/090,113 mailed Jan. 6, 2016, 18 pages.
Final Office Action for U.S. Appl. No. 14/090,122 mailed Apr. 22, 2016, 13 pages.
Final Office Action for U.S. Appl. No. 14/145,027 mailed Nov. 19, 2015, 12 pages.
Final Office Action for U.S. Appl. No. 14/193,294 mailed May 2, 2016, 29 pages.
Final Office Action for U.S. Appl. No. 14/218,326 mailed Jun. 30, 2016, 17 pages.
Final Office Action for U.S. Appl. No. 15/085,166, dated Dec. 4, 2020, 11 pages.
Final Office Action for U.S. Appl. No. 15/137,371 mailed Nov. 28, 2018, 24 pages.
Final Office Action for U.S. Appl. No. 15/427,746 mailed Apr. 15, 2019, 9 pages.
Gemmill, Marin, "The price elasticity of demand for prescription drugs: an exploration of demand in different settings", Doctor of Philosophy Thesis submitted to the London School of Economics and Political Science, Jan. 2008, 380 pages, UMI No. U615895, UMI Dissertation Publishing, ProQuest LLC, US.
Google NPL (non-patent literature) Search on "pharmacy payment benefit copay NDC database", retrieved from the Internet at <https://scholar.google.com/scholar?hl=en&as_sdt-3,47&g-pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
Google Patents Search (including Web Search History, Prior Art Search Printable History Generator) on "pharmacy payment benefit copay NDC database) (prescription) (code) (refills) (error code) country: US before:filing:Dec. 31, 2013", retrieved from the Internet at <https://patents.google.com/?q=pharmacy+payment+benefit+copay+NDC+database&q-prescription&q=code&q=refills&q=error+code&country=US&before-filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q=pharmacy+payment+benefit+copay+NDC+database+pres . . . > retrieved on Jun. 1, 2022, 3 pages.
How to Estimate the Cost of a Prescription. Pam Olson, Sr. Client Services Executive, Navitus Health Solutions (Year: 2015).
Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.
Kamal, Rabah, et al., "What are the recent and forecasted trends in prescription drug spending?" Peterson-KFF Health System Tracker, Feb. 20, 2019, 19 pages, Peterson Center on Healthcare.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-PRESCRIPTIONS, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 mailed Jan. 14, 2015, 11 pages.
Liu, Shiyong, et al., "Evaluating Cost-Effectiveness of Treatment Options for Diabetes Patients Using System Dynamics Modeling", Proceeding of the 2018 Winter Simulation Conference (WSC), Dec. 9-12, 2018, pp. 2577-2588, IEEE, Gothenburg, Sweden.
Marie Chisholm et al. "Pharmaceutical Manufacturer Assistance Program." Arch Intern Med. vol. 162, Apr. 8, 2002.
Non-Final Office Action for U.S. Appl. No. 12/560,071 mailed Jun. 21, 2012, 11 pages.
Non-Final Office Action for U.S. Appl. No. 12/570,982 mailed Jun. 20, 2012, 10 pages.
Non-Final Office Action for U.S. Appl. No. 14/193,294 mailed Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 mailed Oct. 8, 2010, 9 pages.
Non-final Office Action for U.S. Appl. No. 12/189,650 mailed Jan. 22, 2010, 11 pages.
Non-final Office Action for U.S. Appl. No. 12/189,654 mailed Jan. 22, 2010, 11 pages.
Non-Final Office Action for U.S. Appl. No. 12/388,956 mailed Feb. 3, 2011, 11 pages.
Non-Final Office Action for U.S. Appl. No. 12/415,062 mailed Mar. 30, 2011, 23 pages.
Non-Final Office Action for U.S. Appl. No. 12/555,589 mailed Dec. 9, 2011, 12 pages.
Non-Final Office Action for U.S. Appl. No. 12/560,071 mailed Sep. 23, 2014, 17 pages.
Non-Final Office Action for U.S. Appl. No. 12/570,982 mailed Sep. 12, 2013, 22 pages.
Non-Final Office Action for U.S. Appl. No. 12/730,015 mailed Mar. 6, 2012, 9 pages.
Non-Final Office Action for U.S. Appl. No. 12/956,411 mailed Jan. 24, 2011, 9 pages.
Non-Final Office Action for U.S. Appl. No. 12/978,898 mailed Feb. 6, 2013, 12 pages.
Non-Final Office Action for U.S. Appl. No. 12/982,395 mailed Dec. 11, 2012, 13 pages.
Non-Final Office Action for U.S. Appl. No. 13/721,890 mailed Jan. 9, 2015, 11 pages.
Non-Final Office Action for U.S. Appl. No. 13/721,890 mailed Jun. 14, 2016, 9 pages.
Non-final Office Action for U.S. Appl. No. 13/782,909 mailed Feb. 11, 2016, 17 pages.
Non-Final Office Action for U.S. Appl. No. 13/827,676 mailed Dec. 26, 2014, 13 pages.
Non-final Office Action for U.S. Appl. No. 13/827,676 mailed Dec. 30, 2015, 23 pages.
Non-Final Office Action for U.S. Appl. No. 14/145,027 mailed Mar. 23, 2015, 13 pages.
Non-Final Office Action for U.S. Appl. No. 15/137,371 mailed May 29, 2018, 19 pages.
Non-Final Office Action for U.S. Appl. No. 15/427,746 mailed Oct. 18, 2018, 9 pages.

(56) References Cited

OTHER PUBLICATIONS

Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 mailed Mar. 26, 2021, 45 pages.
Non-Final Office Action received for U.S. Appl. No. 16/832,318 mailed Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 mailed Jul. 19, 2010, 13 pages.
Notice of Allowance for U.S. Appl. No. 12/140,015 mailed Jun. 10, 2011, 10 pages.
Notice of Allowance for U.S. Appl. No. 12/165,221 mailed Nov. 16, 2010, 6 pages.
Notice of Allowance for U.S. Appl. No. 12/189,650 mailed Aug. 13, 2010, 11 pages.
Notice of Allowance for U.S. Appl. No. 12/388,956 mailed Jun. 14, 2011, 9 pages.
Notice of Allowance for U.S. Appl. No. 12/956,411 mailed Aug. 5, 2011, 8 pages.
Notice of Allowance for U.S. Appl. No. 12/982,395 mailed Apr. 24, 2013, 9 pages.
Notice of Allowance for U.S. Appl. No. 14/181,011 dated May 15, 2019, 9 pages.
Notice of Allowance for U.S. Appl. No. 15/137,371 mailed May 2, 2019, 11 pages.
Notice of Allowance for U.S. Appl. No. 15/427,746 mailed Dec. 4, 2019, 5 pages.
Notice of Allowance for U.S. Appl. No. 15/427,746 mailed Jul. 31, 2019, 8 pages.
Notice of Allowance received for U.S. Appl. No. 14/643,468, Oct. 24, 2018, 22 pages.
Notice of Allowance received for U.S. Appl. No. 14/181,011, Feb. 13, 2019, 9 pages.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.
Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 mailed Apr. 8, 2015, 9 pages.
Office Action for U.S. Appl. No. 13/782,909 mailed Jun. 25, 2015, 16 pages.
Office Action for U.S. Appl. No. 13/804,175 mailed Mar. 13, 2015, 9 pages.
Office Action for U.S. Appl. No. 14/090,113 mailed Jun. 18, 2015, 14 pages.
Office Action for U.S. Appl. No. 14/090,122 mailed Oct. 21, 2016, 12 pages.
Office Action for U.S. Appl. No. 14/090,122 mailed Sep. 11, 2015, 10 pages.
Office Action for U.S. Appl. No. 14/181,011 mailed Feb. 29, 2016, 23 pages.
Office Action for U.S. Appl. No. 14/181,011 mailed Mar. 20, 2017, 28 pages.
Office Action for U.S. Appl. No. 14/181,011 mailed Oct. 20, 2016, 28 pages.
Office Action for U.S. Appl. No. 14/181,011 mailed Sep. 12, 2017, 17 pages.
Office Action for U.S. Appl. No. 14/193,294 mailed Dec. 17, 2015, 21 pages.
Office Action for U.S. Appl. No. 14/218,326 mailed Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 mailed May 31, 2018, 11 pages.
PTAB Decision on Request for Rehearing for U.S. Appl. No. 14/145,027 mailed Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Scientific and Technical Information Center, Report of Information from Dialog (NPL (non-patent literature) Search Results, Abstracts only), dated Nov. 1, 2021, (Year: 2021), 9 pages.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
Tiriveedhi, V., "Impact of Precision Medicine on Drug Repositioning and Pricing: a Too Small to Thrive Crisis", Journal of Personalized Medicine, Nov. 5, 2018, 11 pages, vol. 8, No. 36, MDPI, Switzerland.
U.S. Notice of Allowance received for U.S. Appl. No. 16/819,258, dated Nov. 16, 2020, 8 pages, U.S.
U.S. Appl. No. 14/229,043, "Systems and Methods for Monitoring and Reporting Redemption Information at a Pharmacy for Patient Incentive Information Identified at the Time of Prescribing," Unpublished (filed Mar. 28, 2014), (Roger Pinsonneault, Inventor), (McKesson Corporation, Assignee), abandoned.
U.S. Appl. No. 15/084,034, "Prescription Provider System," Unpublished (filed Mar. 29, 2016), (Scott Genone, Inventor), (McKesson Corporation, Assignee), abandoned.

(56) References Cited

OTHER PUBLICATIONS

U.S. Appl. No. 16/816,460, "Adaptive System and Method for Adjudicating Claims to Reduce Member Responsibility", Unpublished (Filing Date Mar. 12, 2020), (Michael Rea, Inventor), (RC Savings, LLC, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
U.S. Appl. No. 17/144,426, "Method, Apparatus, and Computer Program Product for Estimating a Target Quantitative Measure Based Upon Historical Electronic Messages," Unpublished (filed Jan. 8, 2021), (Stewart Aragon, et al., Inventor) (McKesson Corporation, Assignee), pending.
U.S. Appl. No. 17/158,118, "Method, Apparatus, and Computer Program Product for Estimating a Target Quantitative Measure Based Upon Historical Electronic Messages," Unpublished (filed Jan. 26, 2021), (Stewart Aragon, et al., Inventor) (McKesson Corporation, Assignee), pending.
U.S. Appl. No. 17/162,461, "Method, Apparatus, and Computer Program Product for Constructing Electronic Message Responses Dependent Upon Historical Information," Unpublished (filed Jan. 19, 2021), (Stewart Aragon, et al., Inventor) (McKesson Corporation, Assignee), pending.
U.S. Appl. No. 17/175,939, "Method, Apparatus, and Computer Program Product for Generating Inquiries in Different Formats, and Compiling Different Information Types in a Response," Unpublished (filed Feb. 15, 2021), (Stacy Hopkins, et al., Inventor) (McKesson Corporation, Assignee), pending.
U.S. Appl. No. 17/499,976, "Method, Apparatus, and Computer Program Product for Providing Real-Time Pricing Information," Unpublished (filed Oct. 13, 2021), (Stacy Hopkins, et al., Inventor) (McKesson Corporation, Assignee), pending.
U.S. Appl. No. 17/501,532, "Method, Apparatus, and Computer Program Product for Providing Real-Time Pricing Information," Unpublished (filed Oct. 14, 2021), (Keith Crozier, et al., Inventor) (McKesson Corporation, Assignee), pending.
U.S. Appl. No. 17/675,616, "Method, Apparatus, and Computer Program Product for Reformatting an Electronic Prescription Transaction," Unpublished (filed Feb. 18, 2022), (Phillip Draa, et al., Inventor) (McKesson Corporation, Assignee), pending.
U.S. Appl. No. 17/676,437, "Method, Apparatus, and Computer Program Product for Partitioning Prescription Transaction Costs in an Electronic Prescription Transaction," Unpublished (filed Feb. 21, 2022), (Phillip Draa, et al., Inventor) (McKesson Corporation, Assignee), pending.
U.S. Appl. No. 18/098,150, "Systems and Methods for Determining and Communicating Patient Incentive Information to a Prescriber," Unpublished (filed Jan. 18, 2023), (Roger G. Pinsonneault, Inventor) (McKesson Corporation, Assignee), pending.
U.S. Appl. No. 18/138,414, "Method, Apparatus, and Computer Program Product for Providing Real-Time Pricing Information," Unpublished (filed Apr. 24, 2023), (Stacy McCrommon, et al., Inventor) (McKesson Corporation, Assignee), pending.
U.S. Appl. No. 18/937,895, "Method, Apparatus, and Computer Program Product for Providing Real-Time Pricing Information and Rerouting Electronic Transactions," Unpublished (filed Nov. 5, 2024), (Stacy McCrommon, et al., Inventor) (McKesson Corporation, Assignee), pending.
U.S. Appl. No. 19/053,907, "Method, Apparatus, and Computer Program Product for Evaluating Prescription Transaction in Accordance with a Database", Unpublished (filing date Feb. 14, 2025), (Phillip Draa, Inventor), (McKesson Corporation, Assignee).
U.S. Appl. No. 19/053,939, "Method, Apparatus, and Computer Program Product for Partitioning Prescription Transaction Costs in an Electronic Prescription Transaction", Unpublished (filing date Feb. 14, 2025), (Phillip Draa, Inventor), (McKesson Corporation, Assignee).
United States Patent and Trademark Office, Advisory Action received for U.S. Appl. No. 17/162,461, dated Aug. 24, 2023, 2 pages, US.
United States Patent and Trademark Office, Advisory Action and Examiner-Initiated Interview Summary received for U.S. Appl. No. 17/705,919, dated Jun. 25, 2024, 33 pages, US.
United States Patent and Trademark Office, Advisory Action for U.S. Appl. No. 15/422,184, Jun. 25, 2019, 4 pages, U.S.A.
United States Patent and Trademark Office, Advisory Action for U.S. Appl. No. 15/422,184, Mar. 26, 2020, 5 pages, U.S.A.
United States Patent and Trademark Office, Advisory Action for U.S. Appl. No. 15/925,011, Jan. 31, 2020, 3 pages, U.S.A.
United States Patent and Trademark Office, Advisory Action for U.S. Appl. No. 15/925,948, Jan. 31, 2020, 4 pages, U.S.A.
United States Patent and Trademark Office, Advisory Action received for U.S. Appl. No. 16/453,509, dated Oct. 12, 2021, 5 pages, U.S.
United States Patent and Trademark Office, Advisory Action received for U.S. Appl. No. 16/832,318, dated Jan. 28, 2022, 4 pages, U.S.
United States Patent and Trademark Office, Advisory Action received for U.S. Appl. No. 16/792,413, dated Mar. 10, 2022, 4 pages, US.
United States Patent and Trademark Office, Advisory Action received for U.S. Appl. No. 16/867,286, dated Dec. 6, 2022, 8 pages, US.
United States Patent and Trademark Office, Advisory Action received for U.S. Appl. No. 17/175,939, dated Dec. 22, 2022, 5 pages, US.
United States Patent and Trademark Office, Advisory Action received for U.S. Appl. No. 16/867,286, dated Feb. 6, 2023, 3 pages, US.
United States Patent and Trademark Office, Advisory Action received for U.S. Appl. No. 17/144,426, dated Mar. 3, 2023, 6 pages, US.
United States Patent and Trademark Office, Advisory Action received for U.S. Appl. No. 17/158,118, dated May 26, 2023, 5 pages, U.S.
United States Patent and Trademark Office, Advisory Action received for U.S. Appl. No. 16/816,460, dated Oct. 19, 2023, 3 pages, US.
United States Patent and Trademark Office, Advisory Action received for U.S. Appl. No. 17/144,426, dated Mar. 21, 2024, 5 pages.
United States Patent and Trademark Office, Advisory Action received for U.S. Appl. No. 17/674,366, dated Mar. 22, 2024, 6 pages.
United States Patent and Trademark Office, Advisory Action received for U.S. Appl. No. 16/816,460, dated Aug. 1, 2024, 3 pages, U.S.
United States Patent and Trademark Office, Advisory Action received for U.S. Appl. No. 17/162,461, dated Aug. 19, 2024, 2 pages, U.S.
United States Patent and Trademark Office, Corrected Notice of Allowability received for U.S. Appl. No. 15/085,166, dated Sep. 20, 2021, 6 pages, U.S.
United States Patent and Trademark Office, Examiner Interview Summary received for U.S. Appl. No. 17/144,426, dated Oct. 22, 2024, 8 pages, U.S.
United States Patent and Trademark Office, Examiner Interview Summary received for U.S. Appl. No. 17/158,118, dated Oct. 22, 2024,8 pages, U.S.
United States Patent and Trademark Office, Examiner Interview Summary received for U.S. Appl. No. 18/098,150, dated Nov. 18, 2024, 3 pages, U.S.
United States Patent and Trademark Office, Examiner Interview Summary received for U.S. Appl. No. 17/175,939, dated Dec. 3, 2024, 2 pages, US.
United States Patent and Trademark Office, Examiner's Answer received for U.S. Appl. No. 16/867,286, dated Jun. 28, 2024, 9 pages, US.
United States Patent and Trademark Office, Final Office Action received for U.S. Appl. No. 16/816,460, dated Aug. 10, 2023, 14 pages, U.S.
United States Patent and Trademark Office, Final Office Action received for U.S. Appl. No. 16/453,509, dated Aug. 18, 2021, 16 pages, U.S.
United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
United States Patent and Trademark Office, Final Office Action received for U.S. Appl. No. 16/792,413, dated Jan. 10, 2022, 80 pages, U.S.

(56) References Cited

OTHER PUBLICATIONS

United States Patent and Trademark Office, Final Office Action received for U.S. Appl. No. 17/012,565, dated Jul. 25, 2022, 43 pages, U.S.

United States Patent and Trademark Office, Final Office Action received for U.S. Appl. No. 16/867,286, dated Sep. 8, 2022, 19 pages, U.S.

United States Patent and Trademark Office, Final Office Action received for U.S. Appl. No. 17/175,939, dated Oct. 5, 2022, 30 pages, U.S.

United States Patent and Trademark Office, Final Office Action received for U.S. Appl. No. 17/144,426, dated Dec. 8, 2022, 21 pages, US.

United States Patent and Trademark Office, Final Office Action received for U.S. Appl. No. 17/158,118, dated Mar. 3, 2023, 19 pages, US.

United States Patent and Trademark Office, Final Office Action received for U.S. Appl. No. 17/162,461, dated May 19, 2023, 23 pages, U.S.

United States Patent and Trademark Office, Final Office Action received for U.S. Appl. No. 16/867,286, dated Sep. 19, 2023, 16 pages, US.

United States Patent and Trademark Office, Final Office Action received for U.S. Appl. No. 17/674,366, dated Dec. 15, 2023, 53 pages, US.

United States Patent and Trademark Office, Final Office Action received for U.S. Appl. No. 17/144,426, dated Dec. 19, 2023, 22 pages, US.

United States Patent and Trademark Office, Final Office Action received for U.S. Appl. No. 17/158,118, dated Dec. 19, 2023, 22 pages, US.

United States Patent and Trademark Office, Final Office Action received for U.S. Appl. No. 17/705,919, dated Feb. 28, 2024, 61 pages.

United States Patent and Trademark Office, Final Office Action received for U.S. Appl. No. 17/175,939, dated Mar. 1, 2024, 24 pages.

United States Patent and Trademark Office, Final Office Action received for U.S. Appl. No. 16/816,460, dated May 3, 2024, 22 pages, U.S.

United States Patent and Trademark Office, Final Office Action received for U.S. Appl. No. 17/162,461, dated Jun. 4, 2024, 38 pages, US.

United States Patent and Trademark Office, Final Office Action received for U.S. Appl. No. 17/144,426, dated Dec. 19, 2024, 22 pages, U.S.

United States Patent and Trademark Office, Final Office Action received for U.S. Appl. No. 17/158,118, dated Dec. 19, 2024, 24 pages, US.

United States Patent and Trademark Office, Final Office Action received for U.S. Appl. No. 17/175,939, dated Feb. 13, 2025, 16 pages, US.

United States Patent and Trademark Office, Final Office Action received for U.S. Appl. No. 17/501,532, dated Feb. 19, 2025, 11 pages, US.

United States Patent and Trademark Office, Final Office Action received for U.S. Appl. No. 18/098,150, dated Feb. 27, 2025, 25 pages, US.

United States Patent and Trademark Office, Final Office Action received for U.S. Appl. No. 17/499,976, dated Mar. 3, 2025, 16 pages, US.

United States Patent and Trademark Office, Final Office Action received for U.S. Appl. No. 16/816,460, dated Mar. 7, 2025, 27 pages, US.

United States Patent and Trademark Office, Interview Summary received for U.S. Appl. No. 17/675,616, dated Aug. 15, 2024,8 pages, U.S.

United States Patent and Trademark Office, Miscellaneous Office Action, Restarting Period, received for U.S. Appl. No. 17/175,939, dated Jun. 14, 2023, 23 pages, U.S.

United States Patent and Trademark Office, Non-Final Office Action received for U.S. Appl. No. 17/846,373, dated Apr. 5, 2024, 76 pages.

United States Patent and Trademark Office, Non-Final Office Action received for U.S. Appl. No. 16/792,413, dated Aug. 5, 2021, 32 pages, U.S.

United States Patent and Trademark Office, Non-Final Office Action received for U.S. Appl. No. 15/085,166, dated Jan. 10, 2022, 12 pages, U.S.

United States Patent and Trademark Office, Non-Final Office Action received for U.S. Appl. No. 16/867,286, dated Feb. 22, 2022, 38 pages, U.S.

United States Patent and Trademark Office, Non-Final Office Action received for U.S. Appl. No. 17/012,565, dated Apr. 12, 2022, 19 pages, U.S.A.

United States Patent and Trademark Office, Non-Final Office Action received for U.S. Appl. No. 16/453,509, dated Apr. 28, 2022, 16 pages, U.S.A.

United States Patent and Trademark Office, Non-Final Office Action received for U.S. Appl. No. 16/552,021, dated May 3, 2022, 60 pages, U.S.A.

United States Patent and Trademark Office, Non-Final Office Action received for U.S. Appl. No. 17/175,939, dated May 12, 2022, 48 pages, U.S.A.

United States Patent and Trademark Office, Non-Final Office Action received for U.S. Appl. No. 16/792,413, dated May 24, 2022, 48 pages, US.

United States Patent and Trademark Office, Non-Final Office Action received for U.S. Appl. No. 17/144,426, dated May 31, 2022, 42 pages, US.

United States Patent and Trademark Office, Non-Final Office Action received for U.S. Appl. No. 16/832,318, dated Jun. 8, 2022, 17 pages, US.

United States Patent and Trademark Office, Non-Final Office Action received for U.S. Appl. No. 16/867,286, dated Mar. 31, 2023, 16 pages, US.

United States Patent and Trademark Office, Non-Final Office Action received for U.S. Appl. No. 17/175,939, dated Apr. 26, 2023, 24 pages, US.

United States Patent and Trademark Office, Non-Final Office Action received for U.S. Appl. No. 16/816,460, dated Mar. 3, 2023, 14 pages, U.S.

United States Patent and Trademark Office, Non-Final Office Action received for U.S. Appl. No. 17/674,366, dated Jun. 6, 2023, 75 pages, U.S.

United States Patent and Trademark Office, Non-Final Office Action received for U.S. Appl. No. 17/705,919, dated Aug. 17, 2023, 68 pages, US.

United States Patent and Trademark Office, Non-Final Office Action received for U.S. Appl. No. 17/162,461, dated Oct. 19, 2023, 25 pages, US.

United States Patent and Trademark Office, Non-Final Office Action received for U.S. Appl. No. 16/816,460, dated Dec. 22, 2023, 46 pages, US.

United States Patent and Trademark Office, Non-Final Office Action received for U.S. Appl. No. 17/675,616, dated May 8, 2024, 74 pages, U.S.

United States Patent and Trademark Office, Non-Final Office Action received for U.S. Appl. No. 17/676,437, dated May 9, 2024, 73 pages, U.S.

United States Patent and Trademark Office, Non-Final Office Action received for U.S. Appl. No. 17/674,366, dated Jun. 5, 2024, 54 pages, US.

United States Patent and Trademark Office, Non-Final Office Action received for U.S. Appl. No. 17/144,426, dated Jul. 18, 2024, 19 pages, US.

United States Patent and Trademark Office, Non-Final Office Action received for U.S. Appl. No. 17/158,118, dated Jul. 18, 2024, 22 pages, US.

United States Patent and Trademark Office, Non-Final Office Action received for U.S. Appl. No. 18/098,150, dated Aug. 27, 2024, 61 pages, U.S.

(56) References Cited

OTHER PUBLICATIONS

United States Patent and Trademark Office, Non-Final Office Action received for U.S. Appl. No. 17/501,532, dated Oct. 17, 2024, 37 pages, U.S.
United States Patent and Trademark Office, Non-Final Office Action received for U.S. Appl. No. 17/499,976, dated Oct. 1, 2024, 79 pages, U.S.
United States Patent and Trademark Office, Non-Final Office Action received for U.S. Appl. No. 17/175,939, dated Oct. 24, 2024, 17 pages, U.S.
United States Patent and Trademark Office, Non-Final Office Action received for U.S. Appl. No. 17/144,426, dated Jul. 13, 2023, 17 pages, U.S.
United States Patent and Trademark Office, Non-Final Office Action received for U.S. Appl. No. 17/158,118, dated Jul. 13, 2023, 18 pages, U.S.
United States Patent and Trademark Office, Non-Final Office Action received for U.S. Appl. No. 16/816,460, dated Nov. 21, 2024, 28 pages, US.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
United States Patent and Trademark Office, Non-Final Office Action received for U.S. Appl. No. 17/162,461, dated Feb. 10, 2025, 36 pages, US.
United States Patent and Trademark Office, Non-Final Office Action received for U.S. Appl. No. 18/138,414, dated Feb. 13, 2025, 68 pages, US.
United States Patent and Trademark Office, Notice of Allowability received for U.S. Appl. No. 15/422,184, Nov. 16, 2020, 2 pages, U.S.A.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
United States Patent and Trademark Office, Notice of Allowance received for U.S. Appl. No. 15/422,184, Oct. 13, 2020, 12 pages, U.S.A.
United States Patent and Trademark Office, Notice of Allowance received for U.S. Appl. No. 15/925,948, Nov. 5, 2020, 22 pages, U.S.A.
United States Patent and Trademark Office, Notice of Allowance received for U.S. Appl. No. 15/085,166, dated Sep. 10, 2021, 21 pages, U.S.
United States Patent and Trademark Office, Notice of Allowance received for U.S. Appl. No. 15/085,166, dated Jun. 15, 2022, 18 pages, U.S.
United States Patent and Trademark Office, Notice of Allowance received for U.S. Appl. No. 17/092,705, dated Dec. 23, 2021, 42 pages, U.S.
United States Patent and Trademark Office, Notice of Allowance received for U.S. Appl. No. 16/043,401, dated Aug. 10, 2020, 9 pages, U.S.A.
United States Patent and Trademark Office, Notice of Allowance received for U.S. Appl. No. 17/219,526, dated Feb. 3, 2022, 48 pages, U.S.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Notice of Allowance received for U.S. Appl. No. 16/552,021, dated Oct. 20, 2022, 14 pages, U.S.
United States Patent and Trademark Office, Notice of Allowance received for U.S. Appl. No. 16/832,318, dated Dec. 8, 2022, 26 pages, US.
United States Patent and Trademark Office, Notice of Allowance received for U.S. Appl. No. 17/846,373, dated Jul. 25, 2024, 16 pages, US.
United States Patent and Trademark Office, Notice of Allowance received for U.S. Appl. No. 17/705,919, dated Sep. 3, 2024, 13 pages, USA.
United States Patent and Trademark Office, Notice of Allowance received for U.S. Appl. No. 17/675,616, dated Sep. 25, 2024, 21 pages, USA.
United States Patent and Trademark Office, Notice of Allowance received for U.S. Appl. No. 17/676,437, dated Sep. 25, 2024, 20 pages, USA.
United States Patent and Trademark Office, Office Action for U.S. Appl. No. 15/925,011, Apr. 8, 2020, 17 pages, U.S.A.
United States Patent and Trademark Office, Office Action for U.S. Appl. No. 15/925,948, Mar. 23, 2020, 29 pages, U.S.A.
United States Patent and Trademark Office, Office Action received for U.S. Appl. No. 15/422,184, May 18, 2020, 31 pages, U.S.A.
United States Patent and Trademark Office, Office Action received for U.S. Appl. No. 15/925,011, Oct. 8, 2020, 8 pages, U.S.A.
Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: https://healthpolicy.usc.edu/research/prescription-drug-copayment-coupon-landscape/>, 21 pages.
Viswanthan, Meera, et al., "Interventions to Improve Adherence to Self-administered Medications for Chronic Diseases in the United States," Annals of Internal Medicine, Dec. 4, 2012, retrieved from the Internet at <https://www.acpjournals.org/doi/full/10.7326/0003-4819-157-11-201212040-00538?rfr_dat=cr_pub++0pubmed&url_ver=Z39.88-2003&rfr_id=ori%3Arid%3Acrossref.org> on Jun. 14, 2023, 25 pages.
Wisconsin Physicians Service (WPS) Insurance Corporation, "How to Read Your Explanation of Benefits Chart," Jun. 16, 2012.
www.ncoil.org/news/DrugCards2.doc dated Apr. 2002, 5 pages.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
United States Patent and Trademark Office, Notice of Allowance received for U.S. Appl. No. 18/098,150, dated Oct. 8, 2025, 19 pages, US.
United States Patent and Trademark Office, Examiner's Answer received for U.S. Appl. No. 17/175,939, dated Oct. 27, 2025, 8 pages, US.
United States Patent and Trademark Office, Non-Final Office Action received for U.S. Appl. No. 17/499,976, dated Jul. 2, 2025, 22 pages, US.
United States Patent and Trademark Office, Notice of Allowance and Interview Summary received for U.S. Appl. No. 18/138,414, Jul. 15, 2025, 24 pages, US.

(56) References Cited

OTHER PUBLICATIONS

United States Patent and Trademark Office, Advisory Action received for U.S. Appl. No. 17/501,532, Apr. 18, 2025, 3 pages, U.S.A.
United States Patent and Trademark Office, Notice of Allowance received for U.S. Appl. No. 17/144,426, Apr. 2, 2025, 9 pages, U.S.A.
United States Patent and Trademark Office, Interview Summary received for U.S. Appl. No. 18/138,414, dated May 9, 2025, 2 pages, US.
United States Patent and Trademark Office, Notice of Allowance and Interview Summary received for U.S. Appl. No. 17/501,532, May 23, 2025, 21 pages, US.
United States Patent and Trademark Office, Non-Final Office Action received for U.S. Appl. No. 16/816,460, dated Sep. 8, 2025, 31 pages, US.
United States Patent and Trademark Office, Notice of Allowance received for U.S. Appl. No. 17/501,532, dated Sep. 10, 2025, 11 pages, US.
United States Patent and Trademark Office, Ptab Decision on Appeal received for U.S. Appl. No. 16/867,286, dated Sep. 25, 2025, 19 pages, US.
United States Patent and Trademark Office, Non-Final Office Action received for U.S. Appl. No. 17/178,509, dated Mar. 29, 2023, 14 pages, US.
United States Patent and Trademark Office, Examiner Interview Summary received for U.S. Appl. No. 17/178,509, dated Jun. 14, 2023, 8 pages, US.
United States Patent and Trademark Office, Final Office Action received for U.S. Appl. No. 17/178,509, dated Jul. 11, 2023, 15 pages, ;US.
United States Patent and Trademark Office, Advisory Action received for U.S. Appl. No. 17/178,509, dated Sep. 18, 2023, 4 pages, US.
United States Patent and Trademark Office, Non-Final Office received for U.S. Appl. No. 17/178,509, dated Dec. 8, 2023, 15 pages, US.
United States Patent and Trademark Office, Examiner Interview Summary for U.S. Appl. No. 17/178,509, dated Mar. 7, 2024, 9 pages, US.
United States Patent and Trademark Office, Final Office received for U.S. Appl. No. 17/178,509, dated Mar. 15, 2024, 19 pages, US.
United States Patent and Trademark Office, Advisory Action and Interview Summary received for U.S. Appl. No. 17/178,509, dated Jun. 26, 2024, 5 pages, US.
United States Patent and Trademark Office, Non-Final Office Action received for U.S. Appl. No. 17/178,509, dated Nov. 7, 2024, 13 pages.
United States Patent and Trademark Office, Interview Summary received for U.S. Appl. No. 17/178,509, dated Feb. 4, 2025, 10 pages.
United States Patent and Trademark Office, Final Office Action received for U.S. Appl. No. 17/178,509, dated Feb. 21, 2025, 13 pages.
United States Patent and Trademark Office, Examiner's Answer to Appeal Brief received for U.S. Appl. No. 17/178,509, dated Aug. 15, 2025, 8 pages.
U.S. Appl. No. 17/178,509, "Method, Apparatus, and Computer Program Product for Standardizing an Electronic Message Component", Unpublished (filing date Feb. 18, 2021), (Ashley Proctor, Inventor), (McKesson Corporation, Assignee).
United States Patent and Trademark Office, Final Office Action received for U.S. Appl. No. 17/162,461, dated Aug. 22, 2025, 23 pages.
United States Patent and Trademark Office, Notice of Allowance received for U.S. Appl. No. 17/158,118, dated Aug. 25, 2025, 13 pages.
United States Patent and Trademark Office, Final Office Action received for U.S. Appl. No. 17/499,976, dated Feb. 5, 2026, 36 pages, US.
United States Patent and Trademark Office, Final Office Action received for U.S. Appl. No. 16/816,460, dated Dec. 18, 2025, 29 pages, US.
United States Patent and Trademark Office, Non-Final Office Action received for U.S. Appl. No. 17/162,461, dated Apr. 1, 2026, 28 pages, US.
United States Patent and Trademark Office, Non-Final Office Action received for U.S. Appl. No. 18/937,895, dated May 20, 2026, 46 pages, US.
United States Patent and Trademark Office, Examiner's Interview Summary received for U.S. Appl. No. 17/162,461, dated Jun. 16, 2026, 2 pages, US.
United States Patent and Trademark Office, Non-Final Office Action received for U.S. Appl. No. 19/053,907, dated Jun. 17, 2026, 24 pages, US.
Gabay, Michael, "RxLegal: Pharmacist Gag Clauses", Hospital Pharmacy, published online Sep. 22, 2018, pp. 376-377, vol. 53, No. 6, Sage Journals, US.
Schroeder, Michael C., "Should You Pay Cash for Your Prescription?", US News & World Report, Health, Jan. 23, 2018, available on the Internet at https://health.usnews.com/health-care/patient-advice/articles/2018-01-23/should-you-pay-cash-for-your-prescription, 4 pages.
United States Patent and Trademark Office, Non-Final Office Action received for U.S. Appl. No. 17/499,976, dated Jun. 29, 2026, 27 pages, US.
Unknown Author, "When Should Patients Pay Cash for Prescriptions", Pharmacy Times, Jun. 30, 2016, available on the Internet at https://www.pharmacytimes.com/view/when-should-patients-pay-cash-for-prescriptions, 2 pages.

* cited by examiner

METHOD, APPARATUS, AND COMPUTER PROGRAM PRODUCT FOR USING MACHINE LEARNING TO GENERATE AN OFFSET AMOUNT

TECHNOLOGICAL FIELD

Embodiments of the present invention relate generally to processing inquiry data objects received over a network, and, more particularly, to methods, apparatuses, and computer program products for using machine learning to generate an offset amount based on longevity, historical data, and associated adherence.

BACKGROUND

The ever changing and complex system relating to prescription drug pricing, and insurance coverage thereof often affects a patient's adherence to a prescription. In some instances, patients may begin to self-manage their care due to the cost of a prescription drug and the associated refills. Especially for expensive prescriptions, a patient might stretch their use of the prescription drug by using the drug less frequently than prescribed to delay incurring the cost of a refill, based on their knowledge of the price they previously paid for the prescription. In some instances, when a prescription drug is prescribed without refills, or without the intent for long-term use, the patient will use the drug as prescribed for the short term, with less thought about the cost, and/or less temptation to delay, prolong, or otherwise alter the prescribed dosage and/or frequency.

BRIEF SUMMARY

Methods, apparatuses, and computer program products are therefore provided for generating an offset amount based on longevity, historical data, and associated adherence. Example embodiments, by use of a computer-implemented model and machine learning algorithms, may identify correlations that reflect higher price sensitivity for products with a longer longevity in comparison to products with a shorter longevity. In this regard, example embodiments utilize a computer-implemented model and machine learning algorithms to improve patient adherence to prescriptions, by dynamically generating offset amounts that may differ dependent on a longevity indicator, or number of refills.

A computer-implemented method is provided for dynamically generating an offset amount based on longevity, historical data and associated adherence. The computer-implemented method includes receiving from a client device, an inquiry data object comprising at least a product identifier and a longevity indicator, and determining a base quantitative amount dependent on at least the product identifier. The computer-implemented method further includes performing an offset calculation protocol to generate the offset amount by which to offset the base quantitative amount, wherein the offset calculation protocol utilizes at least the product identifier and the longevity indicator, and transmitting the base quantitative amount and the offset amount to the client device.

In certain embodiments, determining the base quantitative amount comprises generating and transmitting a prescription benefit inquiry to a third party computer and receiving a prescription benefit inquiry response comprising the base quantitative amount. The base quantitative amount may therefore not be dependent on the longevity indicator.

The computer-implemented method may further include modeling a plurality of inquiry data objects from a plurality of client devices in a network, each inquiry data object comprising a respective product identifier, a respective longevity, a respective quantitative amount, and respective adherence data, wherein the quantitative amounts and the longevity are predictors of the adherence data, and wherein performing the offset calculation protocol comprises applying the inquiry data objects to the model to calculate the offset amount such that a predicted associated adherence data for at least one inquiry data object is improved relative to a predicted associated adherence data with no offset amount.

An offset amount for one inquiry data object may be different from another offset amount calculated for another inquiry data object having common product identifiers, common base quantitative amounts, and different longevities. The computer-implemented method may further include adjusting the offset amount based on an offset limitation.

An apparatus for dynamically generating an offset amount based on longevity, historical data and associated adherence, is provided, the apparatus comprising at least one processor and at least one memory including computer program code, the at least one memory and the computer program code configured to, with the processor, cause the apparatus to at least receive from a client device, an inquiry data object comprising at least a product identifier and a longevity indicator. The memory and computer program code made by further configured to determine a base quantitative amount dependent on at least the product identifier, and perform an offset calculation protocol to generate the offset amount by which to offset the base quantitative amount, wherein the offset calculation protocol utilizes at least the product identifier and the longevity indicator. The memory and computer program code made by further configured to transmit the base quantitative amount and the offset amount to the client device.

The at least one memory and the computer program code are further configured to, with the processor, cause the apparatus to at least model a plurality of inquiry data objects from a plurality of client devices in a network, each inquiry data object comprising a respective product identifier, a respective longevity, a respective quantitative amount, and respective adherence data, wherein the quantitative amounts and the longevity are predictors of the adherence data, and wherein performing the offset calculation protocol comprises applying the inquiry data objects to the model to calculate the offset amount such that a predicted associated adherence data for at least one inquiry data object is improved relative to a predicted associated adherence data with no offset amount.

The at least one memory and the computer program code may be further configured to, with the processor, cause the apparatus to at least adjust the offset amount based on an offset limitation.

A computer program product is also provided, for dynamically generating an offset amount based on longevity, historical data and associated adherence. The computer program product includes at least one non-transitory computer-readable storage medium having computer-executable program code instructions stored therein, the computer-executable program code instructions comprising program code instructions to receive from a client device, an inquiry data object comprising at least a product identifier and a longevity indicator. The computer-executable program code instructions further comprise program code instructions to determine a base quantitative amount dependent on at least the product identifier, and perform an offset calculation protocol to generate the offset amount by which to offset the base quantitative amount, wherein the offset calculation protocol utilizes at least the product identifier and the longevity indicator. The computer-executable program code instructions further comprise program code instructions to transmit the base quantitative amount and the offset amount to the client device.

According to certain embodiments, the computer-executable program code instructions further comprise program code instructions to model a plurality of inquiry data objects from a plurality of client devices in a network, each inquiry data object comprising a respective product identifier, a respective longevity, a respective quantitative amount, and respective adherence data, wherein the quantitative amounts and the longevity are predictors of the adherence data, and wherein performing the offset calculation protocol comprises applying the inquiry data objects to the model to calculate the offset amount such that a predicted associated adherence data for at least one inquiry data object is improved relative to a predicted associated adherence data with no offset amount.

According to certain embodiments, the computer-executable program code instructions further comprise program code instructions to adjust the offset amount based on an offset limitation.

An apparatus is also provides with means for receiving from a client device, an inquiry data object comprising at least a product identifier and a longevity indicator, and means for determining a base quantitative amount dependent on at least the product identifier. The apparatus further includes means for performing an offset calculation protocol to generate the offset amount by which to offset the base quantitative amount, wherein the offset calculation protocol utilizes at least the product identifier and the longevity indicator, and means for transmitting the base quantitative amount and the offset amount to the client device.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
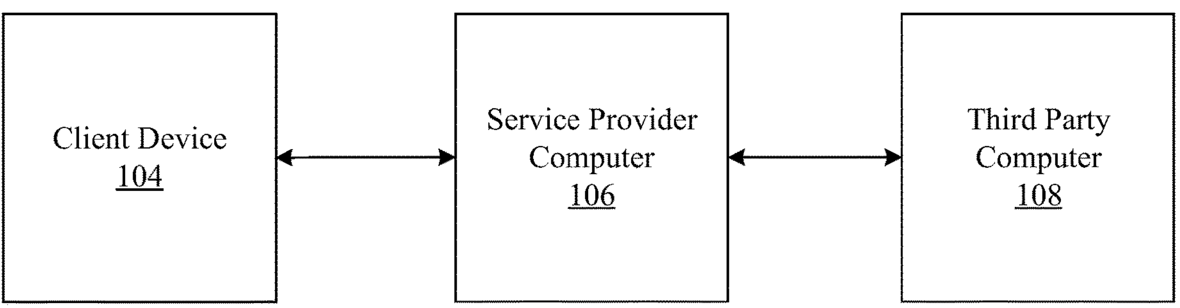
Figure 2:
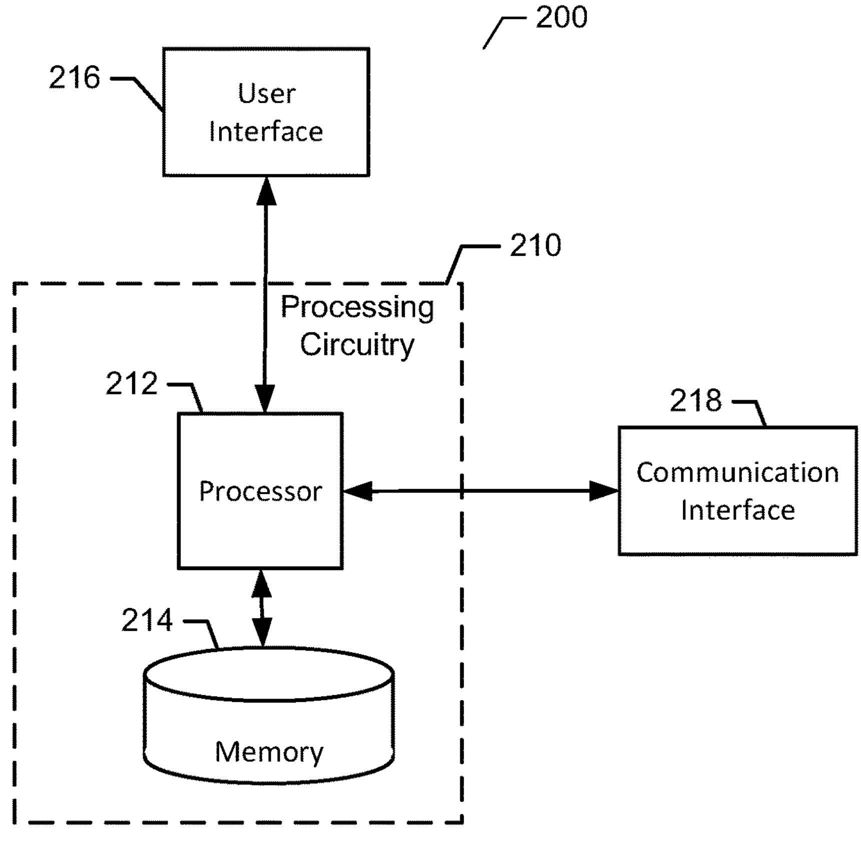
Figure 3:
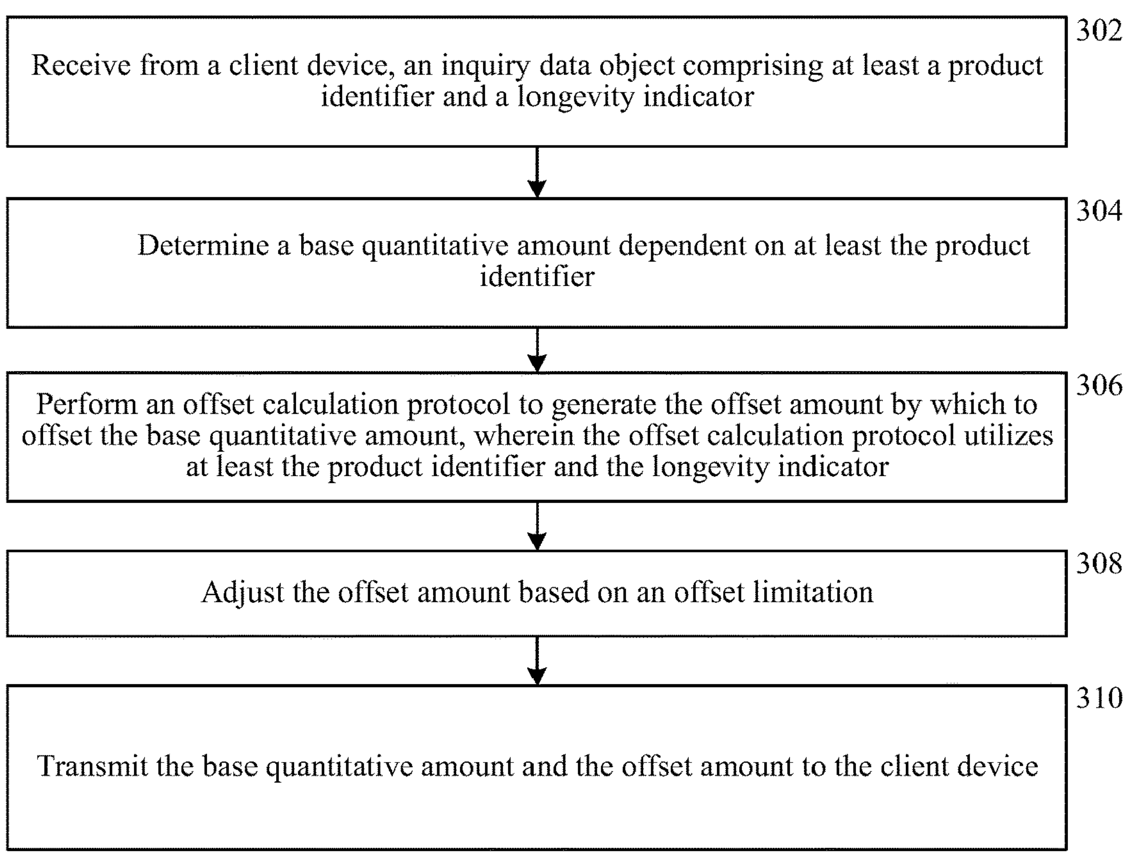
Figure 4:
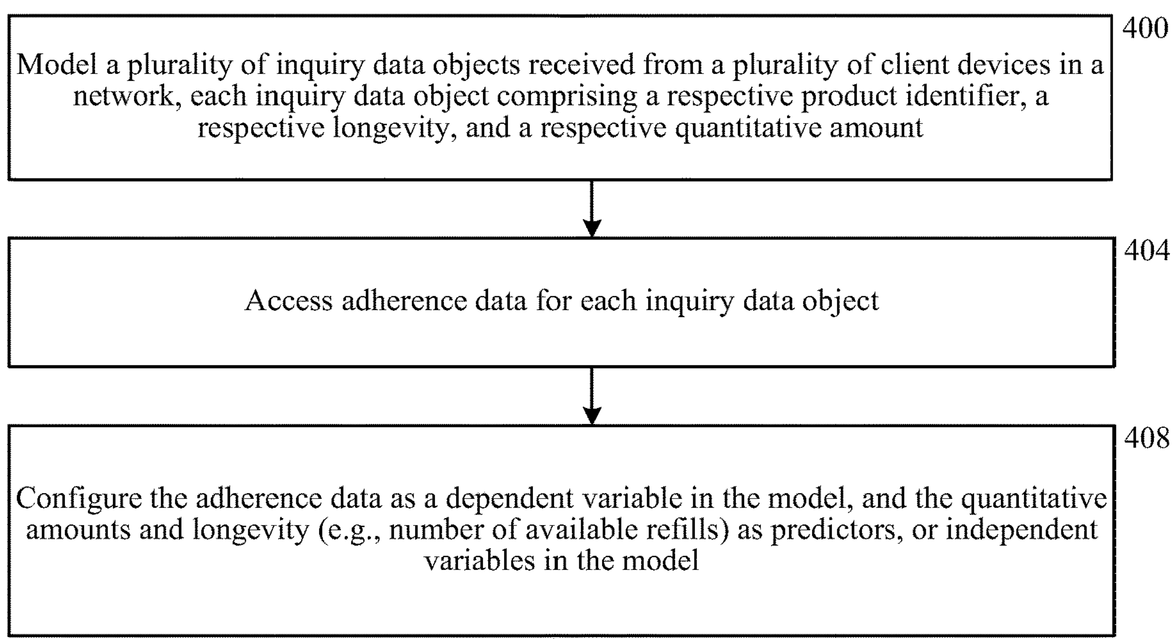

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIGS. 3 and 4 are flowcharts of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to generate an offset amount according to example embodiments described herein. The client device 104 may be a pharmacy computer, such as one associated with a pharmacy or pharmacy network to facilitate the filling of prescriptions, transmitting health insurance claims to a service provider computer 106, and/or the like. The client device 104 may additionally or alternatively be associated with a prescriber, such as a physician's office, clinic, long-term care facility, hospital, etc. Accordingly, while the exemplary client device 104 may be frequently referenced herein as part of a pharmacy or pharmacy network, the client device 104 may be associated with any other healthcare provider, such as a physician's office, hospital and/or other medical facility.

The client device 104 may be any processor-driven device that facilitates the submission of prescription inquiries and/or prescription transaction requests made on behalf of patients or consumers and the communication of information associated therewith to the service provider computer 106. In certain example embodiments, the client device 104 may be a point of sale device associated with a pharmacy. In some embodiments, the client device 104 may be a computer by which a prescriber enters prescription details as an inquiry to obtain prescription pricing, such as during a patient encounter. The execution of the computer-implemented instructions by the client device 104 may form a special purpose computer or other particular machine that is operable to facilitate the submission of prescription inquiries, pharmacy transaction requests made by patients, physicians, pharmacists, and/or the like, and the communication of information associated therewith to a service provider computer 106.

The service provider computer 106 may include, but is not limited to, a processor-driven device that is configured for receiving, processing, and fulfilling prescription inquiries from the client device 104 and corresponding responses from the third party computer 108 (described below), relating to prescription inquiries, claims processing, benefits, billing, other healthcare transactions, and/or other related activities. Additionally or alternatively, the service provider computer 106 may be operable to facilitate the receipt, routing, and/or processing of healthcare transactions such as prescription inquiries and/or transactions and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes healthcare transactions such as prescription transactions. For example, the service provider computer 106 may route prescription transactions communicated from the client device 104 to a third party computer 108, such as that associated with a pharmacy benefits manager (PBM), an insurer, or other payer. According to certain embodiments, the third party computer 108 may comprise any other computer system that receives and adjudicates a prescription transaction on behalf of the payer.

The third party computer 108 may further include a manufacturer computer, or drug manufacturer computer, that may provide electronic files and/or data to the service provider computer 106 that is indicative of available rebates, vouchers, or credit amounts, which may be referred to as an offset amount, for particular prescription drugs. According to certain embodiments, at least two third party computers 108 may be utilized for processing of a transaction. For example, the service provider computer 106 may transmit an inquiry related to prescription benefits to a third party computer 108 implemented as a payer computer. Another third party computer 108, such as one implemented as a manufacturer computer, may provider information, such as contractual amounts, regarding prescription drug offset amounts (e.g., rebates, vouchers, credits, and/or the like), to the service provider computer 106. The offset amounts may be paid and/or funded by the manufacturer. In certain embodiments, multiple instances of a payer computer and/or manufacturer may be present.

The service provider computer 106 may reformat healthcare transactions into another form of transaction and modify the recipient information of the reformatted transaction before routing the reformatted transaction to another party, such as a third party computer 108. The service provider computer 106 may also optionally apply edits to at least some of the healthcare transactions.

The service provider computer 106 may transmit responses from the third party computer 108 regarding the prescription transaction to the client device 104. For example, the service provider computer 106 may notify the client device 104 of a co-pay or out-of-pocket costs to be paid by the patient for the prescription and/or the benefit applied to the prescription transaction. According to certain embodiments a response may include an offset amount (e.g., a rebate, voucher or credit amount). In this regard, a message or other notification may be appended to or included in the response transmitted to the client device 104. Any of the aforementioned responses may be provided to the client device 104 together with the prescription transaction response, or the service provider computer 106 may reformat the prescription transaction to include the details of such responses, and transmit the reformatted healthcare transaction back to the client device 104.

Referring now to FIG. 2, apparatus 200 is a computing device(s) configured for implementing client device 104, service provider computer 106, and/or third party computer 108, according to example embodiments.

Apparatus 200 may at least partially or wholly embody or be embodied by any of the client device 104, service provider computer 106, and/or third party computer 108. Apparatus 200 may therefore implement any of the client device 104, service provider computer 106, and/or third party computer 108, in accordance with some example embodiments, or may be implemented as a distributed system that includes any of the client device 104, service provider computer 106, third party computer 108, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the client device 104 (such as when the client device 104 is implemented as a service communicatively connected to a work station or other user device utilized by a pharmacist or other pharmacy employee, physician and/or the like), service provider computer 106, and/or third party computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the client device 104, service provider computer 106, third party computer 108, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as client device 104, service provider computer 106, third party computer 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a client device 104, and/or third party computer 108. Memory 214 may further include reconciliation tables for tracking the healthcare transactions received from the client device 104, and reconciling them with responses received from third party computer 108. The memory 214 may further comprise a database comprising historical prescription transaction information, provided by the client device 104 and/or third party computer 108. For example, the memory 214 may store historical co-pay and/or out-of-pocket cost information of particular prescriptions paid for by particular patients under a healthcare insurance plan. The memory 214 may be modified as described herein, to reformat prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 implemented as the client device 104, the user interface 216 may, in some example embodiments, provide means for user entry of insurance information, details relating to the dispense of a prescription, and/or the like. The user interface 216 may be further configured to display or provide co-pay and/or out-of-pocket costs of prescriptions, and/or offset amounts, such as when apparatus 200 is implemented as a client device 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of client device 104, service provider computer 106, third party computer 108, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., provider computer 104, service provider computer 106, third party computer 108, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving from a client device, an inquiry data object comprising at least a product identifier and a longevity indicator. The inquiry data object may be indicative of a prescription inquiry and/or prescription transaction that may be received from the client device 104, such as following entry by a pharmacist, prescriber, or other user relating to a prescription drug being for a patient. In certain embodiments, the inquiry data object may be in a first predefined format, such as National Council for Prescription Drug Programs (NCPDP) standard format. In this regard, the inquiry data object may include a prescription claim entered by a healthcare provider, such as a pharmacist, and may include one or more of the following information:

Payer ID/Routing Information

Transaction Payer Identifier(s) that designates a destination of the healthcare transaction (e.g., BIN Number, BIN Number and PCN, or BIN Number and Group ID)

Transaction Code

Patient Information

Name (e.g. Patient Last Name, Patient First Name, etc.)

Date of Birth of Patient
Age of Patient
Patient Gender Code
Patient Address (e.g. Street Address, Zip Code, etc.)
Patient Contact Information (e.g. patient telephone number, email address, etc.)
Patient Health Condition Information
Patient Identification Identifier (such as, but not limited to, patient social security number, a subset of the patient social security number, health insurance claim number (HICN), cardholder ID, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Product identifier (e.g., drug identifier and/or National Drug Code (NDC) number)
Prescription/Service Reference Number
Date Prescription Written
Quantity Dispensed
Days' Supply
Diagnosis/Condition
Pricing information for the drug/service/product
Longevity Indicator (e.g., Number of Refills Authorized)
One or more Drug Utilization (DUR) Codes
Date of Service
Intermediary Authorization Field According to certain embodiments, the product identifier may comprise any unique identifier of a prescription medication. The longevity indicator may include a number of refills to available. The inquiry data object may be received at the service provider 106 for further processing as described below.

As shown by operation 304, apparatus 200 may include means, such as processor 212, memory 214, communication interface 218, and/or the like, for determining a base quantitative amount dependent on at least the product identifier. According to certain embodiments, determining a base quantitative amount may comprise transmitting a prescription claim associated with the inquiry data object to a third party computer 108, such as a payer computer. Example embodiments may access a routing table or other data to determine a recipient third party computer 108 to which to transmit a prescription claim. In this regard, example embodiments may generate the prescription claim from information provided in the inquiry data object, or forward the inquiry data object to the third party computer 108 accordingly. The prescription claim may be transmitted to the third party computer 108 in real-time or near real-time in response to receiving the inquiry data object from the client device 104.

Once received from the service provider computer 106, the third party computer 108 may process the prescription claim and generate a benefit response message. For example, the third party computer 108 may adjudicate the prescription claim, such as according to plan policies. The third party computer 108 may access prior claim details for the patient, and/or amounts previously paid by the patient to determine whether the deductible has been met. In this regard, the third party computer 108 may include in the benefit response message the benefit amount and/or remaining balance owed for the prescription identified in the prescription claim, which may referred to as the base quantitative amount, and may be exclusive of any manufacturer-paid or manufacturer-funded offset, (e.g., rebates, vouchers, credits, and/or the like), described in further detail below. The benefit response message may be appended to or incorporated with the prescription claim, such that when received by the service prover computer 106, the service provider computer 106 can identify the source of the response as associated with the originating inquiry data object received in operation 302. The processed, or adjudicated claim, may be transmitted back to the service provider computer 106 as an adjudicated prescription claim transaction. As set forth above, the adjudicated prescription claim transaction comprising the base quantitative amount may be provided based on at least a determination of whether a deductible has been met. In this regard, the base quantitative amount received in the adjudicated prescription claim transaction may be considered an initial co-pay amount as indicated by the third party computer 108, such as a payer computer, and may be further reduced as set forth below according to certain example embodiments. In certain embodiments, the base quantitative amount is not dependent on, or is independent of, the longevity indicator (e.g., the number of refills).

As shown by operation 306, apparatus 200 may include means, such as processor 212, memory 214, and/or the like, for performing an offset calculation protocol to generate the offset amount by which to offset the base quantitative amount, wherein the offset calculation protocol utilizes at least the product identifier and the longevity indicator. In this regard, certain drug manufacturers may allocate offset amounts (e.g., rebates, vouchers, credits, and/or the like). According to certain embodiments, performing the offset calculation protocol comprises applying the inquiry data object to a model to calculate the offset amount such that a predicted associated adherence data for at least one inquiry data object is improved relative to a predicted associated adhere data with no offset amount.

The model may be implemented by various means, such as but not limited to building the model with historical data over a period of time, such as illustrated in FIG. 4. In operation 400, apparatus 200 may include means, such as processor 212, memory 214, and/or the like, for modeling a plurality of inquiry data objects received from a plurality of client devices in a network, each inquiry data object comprising a respective product identifier, a respective longevity indicator, and a respective quantitative amount (e.g., a patient pay amount, or out-of-pocket cost). In this regard, as the service provider computer 106 functions as a switch to receive, process and route inquiry data objects, and corresponding prescription claims, the service provider computer 106 stores and tracks inquiry data objects, and/or associated prescription claims, over a period of time. The data modeled by the service provider computer 106 may include quantitative amounts associated with the prescription drug, which may include the actual out-of-pocket cost paid by a patient for the prescription, regardless of whether an offset amount (e.g., rebates, vouchers, credits, and/or the like) was applied.

The model may comprise any statistical model implemented by computer program code. For example, the model may include a linear regression model, polynomial regression model, logistic regression model, and/or the like. As the data is received by the service provider computer 106, the data is populated in the model so that statistical analysis, such as that performed by processor 212, driven by computer program code stored on memory 214, can be performed to identify patterns and correlations, and optimize certain inputs to achieve target outputs. It will be appreciated that any statistical model, such as but not limited to a standard model provided by third party services may be utilized, and especially configured as described herein.

In operation 404, apparatus 200 may include means, such as processor 212, memory 214, and/or the like, for accessing adherence data for each prescription and/or inquiry data object. As the service provider computer 106 functions as a switch for prescription transactions and associated inquiry data objects, the service provider computer 106 tracks and stores information relating to patient abandonment of a prescription, how many refills are obtained and/or abandoned, and associated timeframes relating to obtaining the prescription and/or refills. The adherence data may include any information indicative of adherence to the prescription. For example, the adherence information may indicate how many refills out of a total available refills were obtained. The adherence data may therefore include numerical indicators such as 2 of 4, or a percentage such as 50%. In some instances, the adherence data my include a "no refill" indicator, such as for prescriptions that were prescribed for a one-time occurrence or without refills. Prescriptions with refills may, in contrast, be prescribed for long-term or chronic conditions. In this regard, the adherence information may further include multiple instances of a prescription for the same drug and same patient, such as multiple prescriptions over the course of several years, and the associated adherence information. According to certain embodiments, the adherence data may further include and/or reflect timing of the obtained prescription and/or refills. For example, the adherence data may indicate that a patient obtained 2 refills over the period of a year, whereas 3 refills were prescribed. The adherence data may further reflect the elapsed time and/or average elapsed time between refills. In some embodiments, the adherence data may reflect instances in which prescriptions were abandoned at the pharmacy, such as when a patient visits to obtain their prescription, but declines to purchase it, possibly due to the out-of-pocket cost indicated by a pharmacist upon receiving a benefit inquiry response. According to certain embodiments, adherence data may include a reason for abandonment, such as a reason entered by a patient, pharmacist, and/or prescriber. According to certain embodiments, the adherence data may comprise an adherence score that reflects any and/or all available measurements of adherence. For example, both the number of refills and timing of obtaining the refills could be reflected in an adherence score. For example, adherence data for a patient who obtains all refills prior to or on the recommended days (e.g., every 30 days for example), may be assigned an adherence score of 100%, while a patient who obtains all refills but several days late on each refill, may be assigned a lower adherence score such as 80%, for example. A patient who only obtains the first prescription and fails to obtain 3 refills may be assigned an adherence score of only 25%. Various implementations and/or algorithms may be contemplated, with different factors having different weights or significance.

In operation 408, apparatus 200 may include means, such as processor 212, memory 214, and/or the like, for configuring the adherence data as a dependent variable in the model, and the quantitative amounts and longevity (e.g., number of available refills) as predictors, or independent variables in the model. According to certain embodiments and/or scenarios, a user may indicate that the quantitative amounts and longevity are the indicators of adherence data. However, in certain embodiments, the model may be utilized by machine learning algorithms to identify the quantitative amounts and longevity as being the strongest indicators of adherence data. For example, the model may automatically perform training of the model with the historical data including the inquiry data objects, and the corresponding adherence data accessed and applied to the model. The service provider computer 106 may therefore utilize the trained model to identify certain prices, quantitative amounts, and/or ranges, and which for certain longevity indicators (e.g., number of refills), the best adherence data can be obtained. In this regard, the model can be used to predict adherence data for newly received inquiry data for which a base quantitative amount is determined, such as that received in operation 302, by applying the inquiry data object to the model to calculate the offset amount such that a predicted associated adherence data for at least one inquiry data object is improved relative to a predicted associated adherence data with no offset amount. The service provider computer 106 can therefore use the model to perform an offset calculation protocol to generate the offset amount by which to offset the base quantitative amount. For example, if the base quantitative amount, such as an out-of-pocket cost to be paid by a patient for a particular prescription that has 3 refills available is $100, but the service provider computer 106 determines a target quantitative amount of $50 in order to optimize, or improve, predicted adherence data, the service provider computer 106 may generate the offset amount as $50. In contrast, due to the model learning that the longevity is an indicator or predictor of adherence data, in addition to the quantitative amounts, a patient prescribed the same prescription drug under the same plan, but without refills, may be more willing to pay $100 for the same drug, as it is a one-time occurrence. Thus, even with a higher quantitative amount of $100, the scenario may have similar adherence data as a patient with a quantitative amount of $50 for the same drug, but with 3 refills. In this regard, no offset amount, or possibly a smaller offset amount than $50, may be determined for the prescription with no refills. Accordingly, different offset amounts for the same prescription and under the same plan may have different offset amounts and therefore different patient pay amounts. In this regard, example embodiments differentiate offset amounts (e.g., rebates, vouchers, credits, and/or the like) to account for higher price sensitivity for prescription with longer longevity, in comparison to the price sensitivity of prescriptions with shorter longevity.

As shown by operation 308, which may be optional in certain embodiments, apparatus 200 may include means, such as processor 212, memory 214, and/or the like, for adjusting the offset amount based on an offset limitation, such as one enforced by and/or regulated according to a third party computer 108, such as a manufacturer computer. In this regard, the offset amounts (e.g., rebates, vouchers, credits, and/or the like), may not be unlimited, but rather the service provider computer 106 utilizes the operations described herein to distribute offset amounts in a way that may improve adherence data for multiple patients. In this regard, optimization of adherence rates as described herein may refer to improving the predicted adherence rate for at least one inquiry data object, relative to a predicted adherence rate that would be achieved without applying any offset amount. In this regard, if the third party computer 108 indicates, such as by electronic data files comprising contractual amounts, transmitted to the service computer 106, that a maximum offset amount for a particular prescription drug is $40, according to the example above, in which a base quantitative amount of $100, and a target quantitative amount of $50 is calculated for a patient with 3 refills available, the offset amount may be capped to $40, which would result in an adjusted out-of-pocket cost for the patient being $60.

According to certain embodiments, the offset amount may be paid for by a third party, such as the drug manufacturer. For example, some drug manufacturers may participate in an e-voucher program and/or co-pay assistance program to make their drugs more affordable for patients. In this regard, the third party, such as a drug manufacturer, may have a contractual agreement with a pharmacy associated with the client device 104, and/or the service provider 106, regarding the offset amount that may be applied to a particular prescription drug. Contractual amounts may be stored in a database table, for example, indicating a maximum offset savings amount per patient and/or per prescription to be applied each time the prescription is obtained. As another example, a contractual amount may reflect an average amount per prescription of the drug that may be offered as an offset amount, such that service provider computer 106 determines offset amounts dynamically for different instances in a way that balances the goal of improving adherence data, while not exceeding the average price per prescription set forth by the In any event, as shown by operation 312, apparatus 200 may include means, such as processor 212, memory 214, communication interface 218, and/or the like, for transmitting the base quantitative amount and the offset amount to the client device, such as the client device that transmitted the inquiry data object. The processor 212 may be configured to calculate the remaining patient pay amount by subtracting the offset amount from the base quantitative amount. The result may be an adjusted quantitative amount that a patient will pay for the prescription, to be transmitted to the client device 104 for provision via a user interface, such that the patient pay amount can be communicated to the patient. According to certain embodiments, the apparatus 200 includes means to reformat a prescription benefit inquiry response, such as one returned from a third party computer 108, payer computer, adjudication computer, and/or the like, to further include the generated offset amount. In any event, the apparatus 200 may include means, such as processor 212, memory 214, and/or the like, for causing display of the base quantitative amount and the offset amount, and optionally a calculated patient pay amount via a user device and/or client device 104.

In certain embodiments, the operations of FIGS. 3 and 4 occur in real-time or near real-time, possibly subject to short delays (e.g., 3 seconds or less) due to computer processing times. Performing the operations in real-time or near real-time enable the client device 104, such as a pharmacy computer and/or prescriber computer to provide pricing information in real-time or near real-time as the inquiry data object is provided. In instances in which the client device 104 is implemented as a pharmacy computer, a patient purchasing a prescription in the pharmacy will be credited any potential offset amount such that the out-of-pocket cost is reduced in real-time or near real-time relative to the out of pocket cost without an offset amount, or without the advantages of the claimed embodiments. In this regard, the disclosed operations provide a practical application of generating the offset amount by reducing some patient costs and improving prescription adherence by patients.

In instances in which the client device 104 is implemented as a prescriber computer, the prescriber, such as a physician, receives the pricing information in real-time or near real-time as prescription information is entered, and can discuss pricing information with a patient. When the patient knows the out-of-pocket cost in advance and agrees upon a plan of care with their physician, they may be more likely to adhere to the prescription and care plan.

Implementing the disclosed embodiments with a machine learning algorithm further integrates embodiments into a practical application. For example, in instances in which new formularies and/or prescriptions are introduced, the model can be updated automatically and in real-time or near real-time without user intervention, to analyze and/or learn patterns or correlations between quantitative amounts, longevity indicators, and adherence, for the new drug. Additionally or alternative, changes to pricing structures of certain prescription drugs and/or their coverage under certain plans may be automatically reflected in the model. According to certain embodiments, certain drugs may reflect different pricing tolerance or price sensitivity in comparison to others. For example, drugs often prescribed for mild conditions such as allergies, may reflect higher pricing sensitivity (e.g., reflecting higher abandonment the higher the price) than drugs often prescribed for life-threatening conditions such as cancer, which may have a lower price sensitivity, meaning adherence or abandonment is less impacted by price). In this regard, implementing example embodiments within a model implemented by computer program code, and with computer-implemented machine learning algorithms, enables the service provider computer 106 to generate offset amounts to improve adherence for hundreds or thousands of prescription drugs, and according to a longevity indicator for a particular prescription.

Additionally, example embodiments may conserve or reduce processing resources and memory resources otherwise utilized by the client device 104, service provider computer 106, and/or third party computer 108, to submit, process, and route coordination of benefits claims. For example, a reduction in copay may reduce instances in which a prescription expense or transaction is routed to two or more payers, thereby conserving a variety of system resources. Similarly, example embodiments may conserve or reduce processing resources and memory resources otherwise utilized by the client device 104, service provider computer 106, and/or third party computer 108, to submit, process, and route prescription claim reversals, such as in instances in which the patient decides not to follow through with a prescription transaction due to the higher than expected out-of-pocket costs. Such situations in which the resources expended to determine the out-of-pocket costs are wasted may be reduced by reducing the out-of-pocket costs in accordance with an example embodiment and correspondingly increasing the likelihood that a patient fills a prescription, thereby increasing the percentage of instances in which the expenditure of resources to determine the out-of-pocket costs is useful and worthwhile and results in patient adherence with the prescription.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 3 and 4 illustrate operations of a method, apparatus, and computer program product according to some example embodiments. It will be understood that each operation of the flowcharts or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A computer-implemented method for dynamically generating an offset amount based on longevity, historical data and associated adherence, the computer-implemented method comprising:

generating a model based on a plurality of inquiry data objects from a plurality of client devices in a network, each inquiry data object comprising a respective product identifier, a respective longevity indicator comprising a respective number of refills, a respective quantitative amount, and respective adherence data, wherein the quantitative amounts and the respective number of refills are predictors of the respective adherence data;

receiving from a client device, an inquiry data object comprising at least a product identifier and a longevity indicator comprising a number of refills;

generating and transmitting a prescription benefit inquiry to a third party computer;

receiving, from the third party computer, a prescription benefit inquiry response comprising a base quantitative amount, wherein the base quantitative amount is not dependent on the number of refills;

performing an offset calculation protocol to generate the offset amount by which to offset the base quantitative amount, wherein the offset calculation protocol utilizes at least the product identifier and the number of refills, wherein performing the offset calculation protocol comprises applying the inquiry data objects to the model to calculate the offset amount such that a predicted associated adherence data for at least one inquiry data object is improved relative to a predicted associated adherence data with no offset amount, wherein an offset amount for one inquiry data object is different from another offset amount calculated for another inquiry data object having common product identifiers, common base quantitative amounts, and different numbers of refills; and transmitting the base quantitative amount and the offset amount to the client device, wherein performing the offset calculation protocol, utilizing at least the product identifier and the number of refills, and transmitting the base quantitative amount and the offset amount to the client device results in reduced prescription abandonment and corresponding reduced computer resource consumption otherwise expended in facilitating prescription reversals caused by prescription abandonment, in comparison to prescription abandonment and computer resource consumption expended based on computer-implemented methods that do not perform the offset calculation protocol.

2. The computer-implemented method of claim 1, further comprising:

adjusting the offset amount based on an offset limitation.

3. An apparatus for dynamically generating an offset amount based on longevity, historical data and associated adherence, the apparatus comprising at least one processor and at least one memory including computer program code, the at least one memory and the computer program code configured to, with the at least one processor, cause the apparatus to at least:

generate a model based on a plurality of inquiry data objects from a plurality of client devices in a network, each inquiry data object comprising a respective product identifier, a respective longevity indicator comprising a respective number of refills, a respective quantitative amount, and respective adherence data, wherein the quantitative amounts and the respective number of refills are predictors of the respective adherence data;

receive from a client device, an inquiry data object comprising at least a product identifier and a longevity indicator comprising a number of refills;

generate and transmit a prescription benefit inquiry to a third party computer;

receive, from the third party computer, a prescription benefit inquiry response comprising a base quantitative amount, wherein the base quantitative amount is not dependent on the number of refills;

perform an offset calculation protocol to generate the offset amount by which to offset the base quantitative amount, wherein the offset calculation protocol utilizes at least the product identifier and the number of refills, wherein performing the offset calculation protocol comprises applying the inquiry data objects to the model to calculate the offset amount such that a predicted associated adherence data for at least one inquiry data object is improved relative to a predicted associated adherence data with no offset amount, wherein an offset amount for one inquiry data object is different from another offset amount calculated for another inquiry data object having common product identifiers, common base quantitative amounts, and different numbers of refills; and transmit the base quantitative amount and the offset amount to the client device, wherein performing the offset calculation protocol, utilizing at least the product identifier and the number of refills, and transmitting the base quantitative amount and the offset amount to the client device results in reduced prescription abandonment and corresponding reduced computer resource consumption otherwise expended in facilitating prescription reversals caused by prescription abandonment, in comparison to prescription abandonment and computer resource consumption expended based on apparatuses that do not perform the offset calculation protocol.

4. The apparatus of claim 3, wherein the at least one memory and the computer program code are further configured to, with the at least one processor, cause the apparatus to at least:

adjust the offset amount based on an offset limitation.

5. A computer program product for dynamically generating an offset amount based on longevity, historical data and associated adherence, the computer program product comprising at least one non-transitory computer-readable storage medium having computer-executable program code instructions stored therein, the computer-executable program code instructions comprising program code instructions to:

generate a model based on a plurality of inquiry data objects from a plurality of client devices in a network, each inquiry data object comprising a respective product identifier, a respective longevity indicator comprising a respective number of refills, a respective quantitative amount, and respective adherence data, wherein the quantitative amounts and the respective number of refills are predictors of the respective adherence data;

receive from a client device, an inquiry data object comprising at least a product identifier and a longevity indicator comprising a number of refills;

generate and transmit a prescription benefit inquiry to a third party computer;

receive, from the third party computer, a prescription benefit inquiry response comprising a base quantitative amount, wherein the base quantitative amount is not dependent on the number of refills;

perform an offset calculation protocol to generate the offset amount by which to offset the base quantitative amount, wherein the offset calculation protocol utilizes at least the product identifier and the number of refills, wherein performing the offset calculation protocol comprises applying the inquiry data objects to the model to calculate the offset amount such that a predicted associated adherence data for at least one inquiry data object is improved relative to a predicted associated adherence data with no offset amount, wherein an offset amount for one inquiry data object is different from another offset amount calculated for another inquiry data object having common product identifiers, common base quantitative amounts, and different numbers of refills; and transmit the base quantitative amount and the offset amount to the client device, wherein performing the offset calculation protocol, utilizing at least the product identifier and the number of refills, and transmitting the base quantitative amount and the offset amount to the client device results in reduced prescription abandonment and corresponding reduced computer resource consumption otherwise expended in facilitating prescription reversals caused by prescription abandonment, in comparison to prescription abandonment and computer resource consumption expended based on computer program products that do not perform the offset calculation protocol.

6. The computer program product of claim 5, wherein determining the base quantitative amount comprises generating and transmitting a prescription benefit inquiry to a third party computer and receiving a prescription benefit inquiry response comprising the base quantitative amount.

7. The computer program product of claim 5, wherein the base quantitative amount is not dependent on the number of refills.

8. The computer program product of claim 5, wherein the computer-executable program code instructions further comprise program code instructions to:

adjust the offset amount based on an offset limitation.

* * * * *